United States Patent
Hendry et al.

(10) Patent No.: US 6,238,917 B1
(45) Date of Patent: May 29, 2001

(54) ASYMMETRIC HAMMERHEAD RIBOZYMES

(75) Inventors: Philip Hendry, Leichhardt; Maxine J. McCall, Putney, both of (AU)

(73) Assignee: Commonwealth Scientific Industrial Research Organizaion, Dickson (AU)

( * ) Notice: Subject to any disclaimer, the term of this patent is extended or adjusted under 35 U.S.C. 154(b) by 0 days.

(21) Appl. No.: 09/156,828

(22) Filed: Sep. 18, 1998

Related U.S. Application Data

(63) Continuation of application No. PCT/AU97/00210, filed on Apr. 2, 1997, which is a continuation-in-part of application No. 08/627,033, filed on Apr. 2, 1996, now abandoned.

(51) Int. Cl.[7] .................. A61K 31/7088; A61K 31/712; C07H 21/00; C12N 5/10; C12Q 1/68

(52) U.S. Cl. ..................... 435/325; 435/6; 435/91.31; 435/375; 536/24.3; 536/24.31; 536/24.32; 536/24.5

(58) Field of Search ............... 435/6, 91.31, 375, 435/325, 358, 365, 419, 252.3, 252.33, 254.2; 514/44; 536/24.5, 24.3, 24.31, 24.32

(56) References Cited

U.S. PATENT DOCUMENTS

| | | | |
|---|---|---|---|
| 5,149,796 | * | 9/1992 | Rossi et al. .................. 536/23.2 |
| 5,254,678 | * | 10/1993 | Haseloff et al. .................. 536/23.2 |
| 5,334,711 | * | 8/1994 | Sproat .................. 536/24.5 |

FOREIGN PATENT DOCUMENTS

93/23057 * 11/1993 (WO) .
93/23569 * 11/1993 (WO) .

OTHER PUBLICATIONS

Denman et al. "Different activity of trans–acting hammerhead ribozymes targeted to b–amyloid peptide precursor mRNA by altering the symmetry of helicies I and III" Arch. Biochem. Biophys. 323 (1): 71–78, Oct. 20, 1995.*

* cited by examiner

Primary Examiner—Robert A. Schwartzman
Assistant Examiner—Thomas G. Larson
(74) Attorney, Agent, or Firm—John P. White; Cooper & Dunham LLP

(57) ABSTRACT

This invention is directed to a compound having the formula:

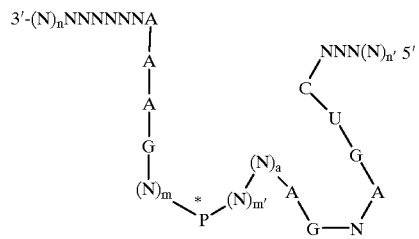

as defined in the detailed description. The compound may be covalently linked to a delivery agent. The invention also includes a composition which comprises the compound in association with an acceptable carrier. The invention also includes a method of cleaving an RNA target sequence which comprises contacting a target sequence with the compound as described above. Further, a method of treating a disease in man or animals associated with a particular RNA which comprises administrating to the man or animal the compound. Further, the invention also includes a diagnostic reagent which comprises the compound.

18 Claims, 7 Drawing Sheets

FIG. 6
Scheme 1
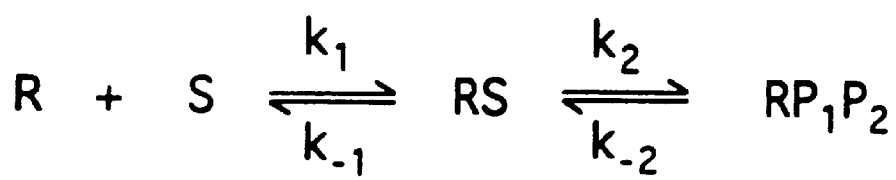
Scheme 2
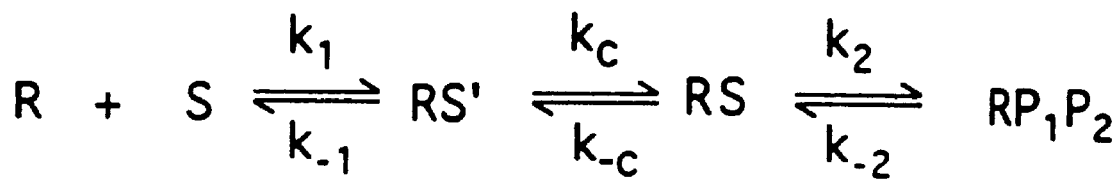

SEQUENCE LISTING

<160> NUMBER OF SEQ ID NOS: 42

<210> SEQ ID NO: 1
<211> LENGTH: 42
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 1
gacacuucau cugaugaguc cuuuuggacg aaacccgcag gt                    42

<210> SEQ ID NO: 2
<211> LENGTH: 42
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 2
gacacttcat cugaugaguc cuuuuggacg aaacccgcag gt                    42

<210> SEQ ID NO: 3
<211> LENGTH: 13
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 3
gcgggucaug aag                                                    13

<210> SEQ ID NO: 4
<211> LENGTH: 21
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 4
accugcgggu caugaagugu c                                           21

<210> SEQ ID NO: 5
<211> LENGTH: 42
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 5
cuccagugug cugaugaguc cuuuuggacg aaacucgcaa at                    42

<210> SEQ ID NO: 6
<211> LENGTH: 42
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 6

```
ctccagtgtg cugaugaguc cuuuuggacg aaactcgcaa at                    42

<210> SEQ ID NO: 7
<211> LENGTH: 38
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 7
agugugcuga ugaguccuuu uggacgaaac ucgcaaat                        38

<210> SEQ ID NO: 8
<211> LENGTH: 21
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 8
auuugcgagu ccacacugga g                                          21

<210> SEQ ID NO: 9
<211> LENGTH: 18
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 9
auuugcgagu ccacacug                                              18

<210> SEQ ID NO: 10
<211> LENGTH: 17
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 10
auuugcgagu ccacact                                               17

<210> SEQ ID NO: 11
<211> LENGTH: 16
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 11
auuugcgagu ccacac                                                16

<210> SEQ ID NO: 12
<211> LENGTH: 15
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 12
```
auuugcgagu ccaca                                                    15

<210> SEQ ID NO: 13
<211> LENGTH: 14
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 13
auuugcgagu ccac                                                     14

<210> SEQ ID NO: 14
<211> LENGTH: 13
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 14
gcgaguccac act                                                      13

<210> SEQ ID NO: 15
<211> LENGTH: 15
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 15
gaguccacac uggag                                                    15

<210> SEQ ID NO: 16
<211> LENGTH: 42
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 16
guccuaggcu cugaugacuc cuuuuggacg aaacuuccug ga                      42

<210> SEQ ID NO: 17
<211> LENGTH: 34
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 17
uaggcucuga ugaguccuuu uggacgaaac uucc                               34

<210> SEQ ID NO: 18
<211> LENGTH: 42
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 18
gtcctaggct cugaugaguc cuuuuggacg aaacuuccug ga                      42

```
<210> SEQ ID NO: 19
<211> LENGTH: 37
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 19
guccuaggcu cugaugaguc cuuuuggacg aaacuuc                              37

<210> SEQ ID NO: 20
<211> LENGTH: 37
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 20
aggcucugau gaguccuuuu ggacgaaacu uccugga                              37

<210> SEQ ID NO: 21
<211> LENGTH: 13
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 21
ggaagucagc cua                                                        13

<210> SEQ ID NO: 22
<211> LENGTH: 21
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 22
tccaggaagu cagccuagga c                                               21

<210> SEQ ID NO: 23
<211> LENGTH: 16
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 23
tccaggaagu cagcct                                                     16

<210> SEQ ID NO: 24
<211> LENGTH: 16
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 24
gaagucagcc uaggac                                                     16
```

```
<210> SEQ ID NO: 25
<211> LENGTH: 14
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 25
tccaggaagu cagc                                                      14

<210> SEQ ID NO: 26
<211> LENGTH: 15
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 26
tccaggaagu cagcc                                                     15

<210> SEQ ID NO: 27
<211> LENGTH: 17
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 27
tccaggaagu cagccua                                                   17

<210> SEQ ID NO: 28
<211> LENGTH: 18
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 28
tccaggaagu cagccuag                                                  18

<210> SEQ ID NO: 29
<211> LENGTH: 19
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 29
tccaggaagu cagccuagg                                                 19

<210> SEQ ID NO: 30
<211> LENGTH: 40
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 30
gcgaugacgu gaugaggccg aaaggccgaa acguucccdt                          40
```

```
<210> SEQ ID NO: 31
<211> LENGTH: 38
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 31
gaugaccuga ugaggccgaa aggccgaaac guucccdt                                38

<210> SEQ ID NO: 32
<211> LENGTH: 14
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 32
gggaacgucg ucdg                                                          14

<210> SEQ ID NO: 33
<211> LENGTH: 15
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 33
gggaacgucg ucgdt                                                         15

<210> SEQ ID NO: 34
<211> LENGTH: 16
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 34
gggaacgucg ucgudc                                                        16

<210> SEQ ID NO: 35
<211> LENGTH: 17
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 35
gggaacgucg ucgucdg                                                       17

<210> SEQ ID NO: 36
<211> LENGTH: 19
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 36
gggaacgucg ucgucgcdc                                                     19

<210> SEQ ID NO: 37
```

```
<211> LENGTH: 14
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 37
gggaacgucg ucda                                                        14

<210> SEQ ID NO: 38
<211> LENGTH: 15
<212> TYPE: DNA
<213> ORGANISM: Artificial Sequence
<220> FEATURE:
<223> OTHER INFORMATION: Description of Artificial Sequence: Ribozymes
      and Portions thereof

<400> SEQUENCE: 38
gggaacgucg ucadt                                                       15

<210> SEQ ID NO: 39
<211> LENGTH: 16
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 39
gggaacgucg ucaudc                                                      16

<210> SEQ ID NO: 40
<211> LENGTH: 17
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 40
gggaacgucg ucaucdg                                                     17

<210> SEQ ID NO: 41
<211> LENGTH: 19
<212> TYPE: RNA
<213> ORGANISM: Artificial Sequence
<220> FEATURE:
<223> OTHER INFORMATION: Description of Artificial Sequence: Ribozymes
      and Portions thereof

<400> SEQUENCE: 41
gggaacgucg ucaucgcdc                                                   19

<210> SEQ ID NO: 42
<211> LENGTH: 35
<212> TYPE: RNA
<213> ORGANISM: Artificial Sequence
<220> FEATURE:
<223> OTHER INFORMATION: Description of Artificial Sequence: Ribozymes
      and Portions thereof
<223> OTHER INFORMATION: n= A, C, G OR T/U.  OTHER OR UNKNOWN

<400> SEQUENCE: 42
nnnnnncuga ugagnnnnnn nnnncgaaan nnnnn                                 35
```

ASYMMETRIC HAMMERHEAD RIBOZYMES

This application is a continuation of PCT International Application No. PCT/AU97/00210, filed Apr. 2, 1997, designating the United States of America which is a continuation-in-part of U.S. patent application Ser. No. 08/627,033, filed Apr. 2, 1996 now abandoned.

Hammerhead ribozymes were discovered as the self-cleaving motifs in a number of small circular plant pathogenic RNAs (Buzayan et al. 1986; Hutchins et al. 1986; Symonds, 1992). Uhlenbeck (Uhlenbeck, 1987) showed that a ribozyme was able to act in a bimolecular fashion, and as a true enzyme on a very specific substrate with defined secondary structure and stringent sequence requirements. Haseloff and Gerlach (Haseloff, et al. 1988) described the division of the hammerhead into a form in which the conserved nucleotides were located on the enzyme strand, the only sequence requirements for the substrate being GUC, just 5' to the cleavage site, this sequence requirement was shown to be too restrictive and only the sequence UH just 5' of the cleavage site was required for activity (Perriman, et al. 1992; Shimayama, et al.1995; Zoumadakis, et al. 1995) (H=A, U or C). Since 1988 this configuration has been the paradigm for the design of hammerhead ribozymes. The cleavage mechanism for the hammerhead ribozyme is usually analyzed according to the conventional enzyme mechanism, i.e. reversible substrate binding, the cleavage step, reversible product dissociation and the product is not consumed in the reaction (Hertel, et al. 1994). The cleavage step has been assumed to be essentially independent of the length and sequence of the helices I and III (Fedor, et al. 1992). The inventors (Hendry, et al. 1995) have made a number of observations which suggest that the cleavage rate constant may be dependent of the length and/or sequence of the helices I and III.

There is a great need for ribozymes that have high catalytic rates. The need for highly effective ribozymes is particularly important for ribozyme compounds with modified oligonucleotides because the cost of the starting materials. While prior workers have prepared hammerhead ribozymes varying the length of both the 5' and 3' hybridizing arms, helices I and III, respectively, (Denman et al. 1995; Ellis, et al. 1993; Fedor et al. 1990; Gast et al. 1994; Homann et al. 1994; Zoumadakis, et al. 1995) this is the first disclosure of specific asymmetric hammerhead compounds showing dramatic rate increases.

SUMMARY OF THE INVENTION

This invention is directed to a compound having the formula:

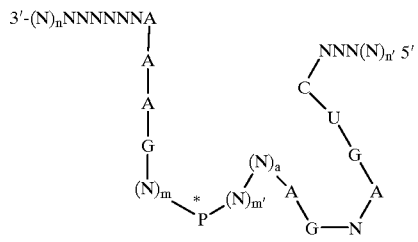

as defined in the detailed description. The compound may be covalently linked to a delivery agent. The invention also includes a composition which comprises the compound in association with an acceptable carrier. The invention also includes a method of cleaving an RNA target sequence which comprises contacting a target sequence with the compound as described above. Further, a method of treating a disease in man or animals associated with a particular RNA which comprises administrating to the man or animal the compound. Further, the invention also includes a diagnostic reagent which comprises the compound.

BRIEF DESCRIPTION OF THE FIGURES

Figure Legends

FIG. 2 Sequences and structures of some Kruppel substrates and ribozymes to exemplify the system of nomenclature. Upper case letters are RNA, lower case letters are DNA. (SEQ ID NOS 5, 7–13, and 15)

FIG. 6 Scheme 1 and 2 showing the steps of the reaction.

DETAILED DESCRIPTION OF THE INVENTION

Figure 1:
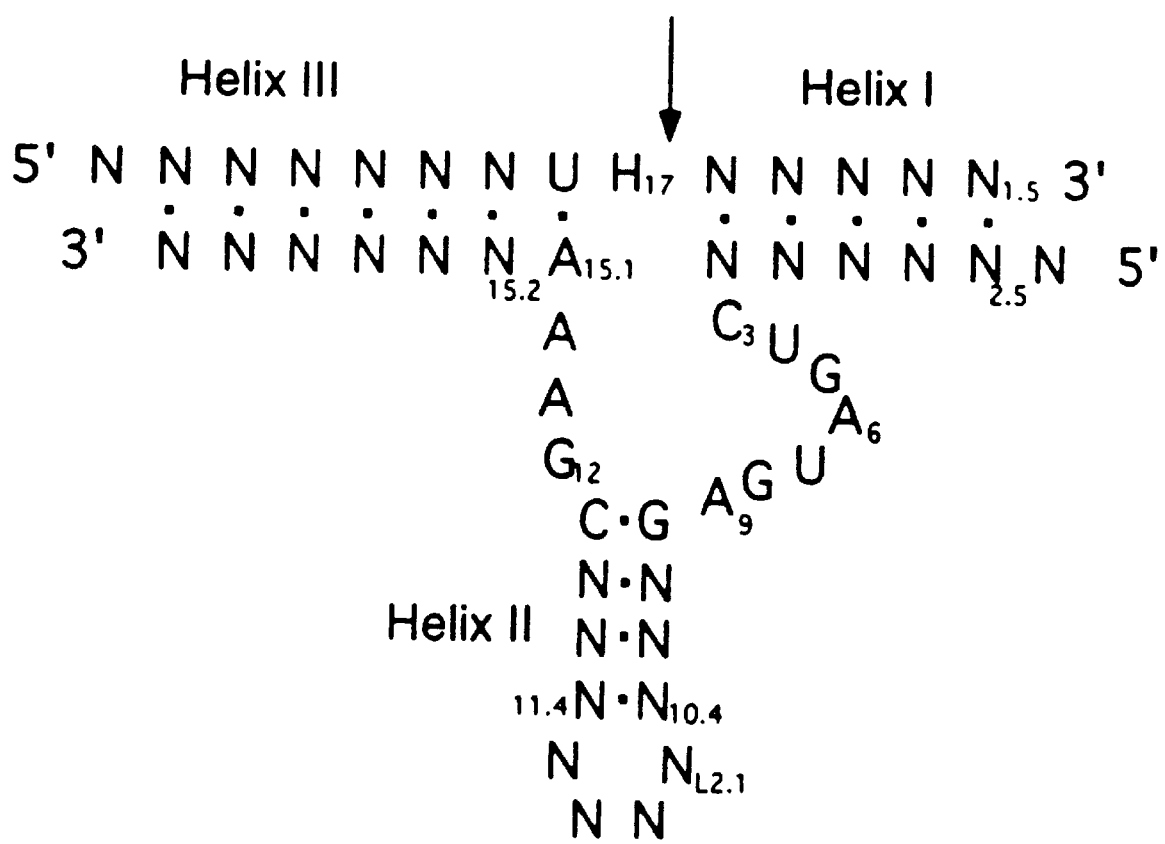
FIG. 1 (SEQ ID NO. 42) Schematic representation of the hammerhead ribozyme in complex with its complementary substrate. The helices formed between the substrate and ribozyme are I and III, helix II is formed within the ribozyme. H=C, U or A, at the cleavage site. Some of the nucleotides are labeled using the numbering system of Hertel et al. (Hertel, et al. 1992).

This invention is directed to a compound having the formula:

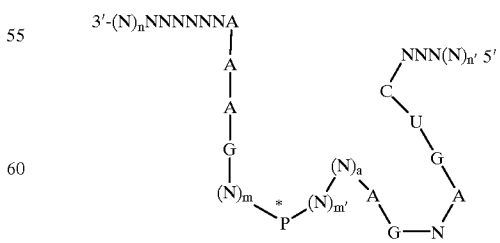

In the compound each N represents a nucleotide which may be the same or different and may be substituted or modified in its sugar, base or phosphate provided not every N is a ribonucleotide. The hybridizing arms 3'-(N)$_n$ NNNNNA and NNN(N)$_{n'}$5' each represent an oligonucleotide having a predetermined sequence which is complementary to an RNA target sequence to be cleaved. In the arms n and n' represents an integer which defines the number of nucleotides in the oligonucleotide with the proviso that n is from 1 to 5 and n' is from 1 to 3 and each * represents base pairing between the nucleotides located on either side thereof. In the compound each solid line represents a chemical linkage providing covalent bonds between the nucleotides located on either side thereof. The symbol "a" represents an integer which defines a number of nucleotides with the proviso that a may be 0 or 1 and if 0, the A located 5' of (N)$_a$ is bonded to the N located 3' of (N)$_a$. In the stem-loop of the compound each m and m' represents an integer which is greater than 2; wherein P represents a non-nucleotide linker or a nucleotide linker (N)$_b$ and wherein (N)$_c$ represents an oligonucleotlde which may be present with the proviso that b represents an integer which Is greater than or equal to 3.

In a preferred embodiment of the invention, the oligonucleotide 3'-(N)$_n$NNNNNNA is 3'-(N)$_n$ NNNNNCA. In another embodiment (N)$_a$ is absent. In the compound of the integer b of (N)$_b$ may be equal to 4 and each of m and m' may be 4.

In one embodiment each N in the compound may be a deoxyribonucleotide. Alternatively, each N of 3 (N)$_n$NNNNNNA and N$_n$NN(N)' 5' may be a deoxyribonucleotide. In yet another embodiment several of the nucleotides N, A, C, G or U are O methyl or O-alkyl ribonucleotides. The RNA target sequence for the compound may be a viral RNA target sequence.

The compound described above may be covalently linked to a delivery agent. The delivery agent is a peptide, a peptide mimic, a cholesterol, a steroid, a cholesterol derivative, a fat, a vitamin, biotin, folic acid, retinoic acid, a protein, ferritin, LDL, insulin, an antibody, a sugar or an oligosaccharide, polyethylene glycol or a homopolymer or co-polymer of aminoacids.

The invention also includes a composition which comprises a compound described above in association with an acceptable carrier. The acceptable carrier may be a cationic lipid, a cholesterol, a cholesterol derivative, a liposome, or a homopolymer or co-polymer of aminoacids.

The invention also included a host cell comprising the compound above which may be a prokaryotic host cell or an eukaryotic host cell. The prokaryotic host may be an *E. coli* host cell. The eukaryotic host cell may be a monkey COS host cell, a Chinese hamster ovary host cell, a mammalian host cell, a plant host cell or yeast cell.

The invention also includes a method of cleaving an RNA target sequence which comprises contacting the target sequence with the compound as described above. Further a method of treating a disease in man or animals associated with a particular RNA which comprises administrating to the man or animal the compound. Further, the invention also includes a diagnostic reagent which comprises the compound.

It is usually the case that substrates which form relatively short helices I and III with hammerhead ribozymes are cleaved more rapidly than substrates which create longer binding helices (see table 1). It may be that one or other of the binding helices was required to be relatively weak to allow rapid conformational changes in the ribozyme-substrate complex. Two independent symmetric (10+10) hammerhead ribozymes were found to cleave substrates which formed a helix I of 5 nucleotides at a rate several orders of magnitude faster than substrates which formed a helix III of 5 nucleotides, the other helix being 10 nucleotides in each case. The phenomenon is observed for both all-RNA and DNA-armed ribozymes. Similar results are obtained when the length of the helices I and III are limited by the length of the hybridizing arms of the rlbozymes; a symmetric 21-mer substrate is cleaved more than 100 fold faster by an asymmetric ribozyme with 5 hybridizing nucleotides in its 5' arm and 10 hybridizing bases in its 3' arm than the converse (10/5) asymmetric ribozyme. Preferred cleavage sites in the target RNA have the sequence "UH," preferably GUC, GUU, GUA, UUA and UUC. By way of example, suitable reaction conditions may comprise a temperature from about 4 degree(s) C. to about 60 degree(s) C., preferably from about 10 degree(s) to 45 degree(s) C., more preferably from about 20 degree(s) to 43 degree(s) C., pH from about 6.0 to about 9.0 and concentration of divalent cation (such as $Mg^{2+}$) from about 0.1 to 100 mM (preferably 0.2 to 20 mM or more preferably 0.5 to 5 mM). The nucleotides of the sequences 3'-(N)$_n$NNNNNNA and NNN$_n$(N) 5' of the compounds above may be of any number and sequence sufficient to enable hybridization with the nucleotides in the target RNA, as described herein. In addition these compounds may be covalently attached to an antisense molecule which may be 10 to 100 bases in length. Antisense sequences capable of hybridizing to an RNA in a mammal or plant are well known see (Shewmaker et al. U.S. Pat. No. 5,107,065, issued Apr. 21, 1992). As the ribozyme acts as an enzyme, showing turnover, the ratio of ribozyme to substrate may vary widely.

A target RINA containing a suitable cleavage site such as UH site may be incubated with the compound described above. The nucleotide sequences 3'-(N)$_n$NNNNNNA and NNN(N)$_{n'}$ 5' of the compounds above are selected to hybridize with their substrate. They may be selected so as to be complementary to nucleotide sequences flanking the cleavage site in the target RNA. On incubation of the ribozyme or ribozyme composition and its substrate, an enzyme/substrate complex is formed as a result of base pairing between corresponding nucleotides in the ribozyme and the substrate. Nucleotide sequences complementary to 3-(N)$_n$NNNNNA and NNN(N)$_{n'}$ 5' of the compounds above flanking the cleavage site in the substrate may form a double stranded duplex through base pairing. This base pairing is well known in the art [See for example: Sambrook, 1989]. The formation of a double stranded duplex between the nucleotides may be referred to as hybridization [Sambrook, 1989]. The extent of hybridization or duplex formation between the ribozyme and its substrate can be readily assessed, for example, by labeling one or both components, such as with a radiolabel, and then subjecting the reaction mixture to polyacrylamide gel electrophoresis under non-denaturing conditions [Sambrook, 1989]. It is preferable that the compounds are complementary with their target. If the target is cleaved specifically on incubation with the compound, the compound is active and falls within the scope of this invention. Accordingly, a ribozyme containing substituted or modified nucleotides in the conserved region may be simply tested for endonuclease activity in a routine manner.

As will be readily appreciated by workers in the field to which this invention relates, the cleavage of a target RNA may be readily assessed by various methods well known in the art [See for example: Sambrook, 1989]. Cleavage may, for example, be assessed by running the reaction products (where the substrate is radioactively labeled) on acrylamide, agarose, or other gel systems under denaturing conditions, and then subjecting the gel to autoradiography or other analytical technique to detect cleavage fragments [Sambrook, 1989].

In another embodiment, the invention provides a composition which comprises the compounds above in association with an acceptable carrier. The invention also provides a host cell containing the compounds above which may be a prokaryotic host cell or an eukaryotic host cell e.g. yeast cell or yeast protoplast, E. coli host cell, a monkey host cell (e.g. COS), a Chinese hamster ovary host cell, a mammalian host cell, a plant host cell, or a plant protoplast host cell.

In another embodiment, the composition, as discussed above, is in association with an acceptable carrier. This invention also provides a composition as discussed hereinabove wherein the oligonucleotide is an RNA-DNA hybrid molecule comprising nucleotides which may be substituted or modified in their sugar, base or phosphate group. It is preferred that the oligonucleotide be a hybrid RNA-DNA molecule. However, other substitutions or modifications n the nucleotide are possible providing that endonuclease activity is not lost. Such derivatives or modifications are described below.

The oligonucleotide compound may comprise deoxyribonucleotides, ribonucleotides, deoxyribonucleotide ribonucleotide hybrids, or nuclectides modified in the sugar, phosphate or base, or an oligonucleotide comprising any mixture thereof. derivatives thereof as herein described. The flanking sequences 3'-$(N)_n$NNNNNNA and NNN$(N)_{n'}$ 5' may be chosen to optimize stability of the ribozyme from degradation. For example, deoxyribonucleotides are resistant to the action of ribonucleases. Modified bases, sugars or phosphate linkages of nucleotides, such as phosphoramidate, or phosphorothioate linkages in the sugar phosphate chain of 31-$(N)_n$NNNNNNA and NNN$(N)_{n'}$ 5', may also provide resistance to nuclease attack. Binding affinity may also be optimized in particular circumstances, by providing nucleotides solely in the form of ribonucleotides, deoxyribonucleotides, or combinations thereof. In some circumstances it may be necessary to optimize the composition of the sequences 3'-$(N)_n$NNNNNNA and NNN$(N)_{n'}$ 5', to maximize target RNA cleavage. The cleavage activity of ribozymes having flanking nucleotide sequences which hybridize to target sequences may be comprised wholly of deoxyribonucleotides. In such circumstances optimization may involve providing a mixture of deoxyribonucleotides and ribonucleotides in the nucleotide sequences 3-$(N)_n$NNNNNNA and NNN$(N)_{n'}$ 5'. For example, nucleotides in the ribozyme which are proximal to the cleavage site in a target RNA may be ribonucleotides.

The respective 3' and 5' termini of the sequences 3-$(N)_n$NNNNNNA and NNN$(N)_{n'}$ 5', or alternatively the 3' and 5' end termini of the ribozyme, may be modified to stabilize the ribozyme from degradation. For example, blocking groups may be added to prevent exonuclease attack, in particular 3'-5' progressive exonuclease activity. By way of example, blocking groups may be selected from substituted or unsubstituted alkyl, substituted or unsubstituted phenyl, substituted or unsubstituted alkanoyl. Substituents may be selected from $C_1$–$C_5$ alkyl; halogens such as F, Cl or Br; hydroxy; amino; $C_1$–$C_5$ alkoxy and the like. Alternatively, nucleotide analogues such as phosphorothioates, methylphosphonates or phosphoramidates or nucleoside derivatives (such as alpha—anomer of the ribose moiety) which are resistant to nuclease attack may be employed as terminal blocking groups. The blocking group may be an inverted linkage such as a 3'—3' thymidine linkage, 3–3' abasic ribose or deoxyribose linkage or a 5'—5' triphosphate linkage as in the guanosine cap.

Alternatively, groups which alter the susceptibility of the ribozyme molecule to other nucleases may be inserted into the 3' and/or 5' end of the ribozyme. For example, 9-aminoacridine attached to the ribozyme may act as a terminal blocking group to generate resistance to nuclease attack on the ribozyme molecules and/or as an intercalating agent to aid endonucleolytic activity of the ribozyme. It will be readily appreciated that a variety of other chemical groups, e.g. spermine or spermidine could be used in a related manner.

The compounds of this invention may be covalently or non-covalently associated with affinity agents such as proteins, steroids, hormones, lipids, nucleic acid sequences, intercalating molecules (such as acridgne derivatives, for example 9-amino acridine) or the like to modify binding affinity for a substrate nucleotide sequence or increase affinity for target cells, or localization in cellular compartments or the like. For example, the ribozymes of the present invention may be associated with RNA binding peptides or proteins which may assist in bringing the ribozyme into juxtaposition with a target nucleic acid such that hybridization and cleavage of the target sequence may take place. Another derivative might be an aptamer which is attached to the compound so that upon the binding to a particular aptamer substrate the ribozyme is activated, in a tissue or cell specific manner (Huizenga et al. 1995). The aptamer may also serve as an affinity agent to localize the ribozyme to particular tissues, cells or cell-compartment e.g. thrombin (Bracht et al. 1995, 1994). Nucleotide sequences may be added to the respective 3' and 5' termini of the sequences 3'-$(N)_n$NNNNNNA and NNN$(N)_{n'}$ 5' or alternatively the 3' and 5' end termini of the ribozyme to increase affinity for substrates. Such additional nucleotide sequences may form triple helices with target sequences [Strobel, 1991] which may enable interaction with an intramolecularly folded substrate. Alternatively, modified bases (non-natural or modified bases as described in Principles of Nucleic Acid Structure [Saenger, 1984]) within the additional nucleotide sequences may be used that will associate with either single stranded or duplex DNA generating base pair, triplet, or quadruplet, interactions with nucleotides in the substrate. Suitable bases would include inosine, 5-methylcytosine, 5-bromouracil and other such bases as are well known in the art, as described, for example, in Principles of Nucleic Acid Structure [Saenger, 1984].

The compounds of this invention may be produced by nucleotide synthetic techniques which are known in the art, and described for example by Carruthers et al., Foehler et al. and Sproat et al. [Carruthers, 1987; Foehler, 1986; Sproat, 1984]. Generally, such synthetic procedures involve the sequential coupling of activated and protected nucleotide bases to give a protected nucleotide chain, whereafter protecting groups may be removed by suitable treatment. Preferably the compounds will be synthesized on an automated synthesizer such as those made by Applied Biosystems (a Division of Perkin Elmer), Pharmacia or Millipore. Alternatively, the ribozymes in accordance with this invention may be produced by transcription of nucleotide sequences encoding said ribozymes in host-cells or in cell free systems utilizing enzymes such as T3, SP6 or T7 RNA-polymerase and made with modified nucleoside triphosphates oligonucleotides or modified after transcription.

The phosphodiester bonds of RNA can be replaced by phosphorothicate linkages by in vitro transcription using nucleoside 5'-O-(1-thiotriphosphates). T7 RNA polymerase specifically incorporates the Sp isomer of α-phosphorthiotriphosphate with inversion of configuration to produce the Rp isomer of the phosphorothioate linkage. The methods to produce transcripts fully substituted with phosphorothioate linkages adjacent to a given nucleotide, or to produce partially substituted transcripts containing approximately one phosphorothioate linkage. The methods to produce transcripts fully substituted with phosphorothicate linkages adjacent to a giver nucleotide, or to produce partially substituted transcripts containing approximately one phosphorothicate linkage per molecule, are described by Ruffner and Uhlenbeck (1990). Conrad et al. (1995) describe methods so using T7 RNA polymerase to produce chimeric transcripts containing ribonucleotides and deoxyribonucleotides (with and without phosphorothioate linkages), and also ribonucleotides and 2'-O-methylnucleotides (with and without phosphorothicate linkages). These methods have been shown to produce transcripts containing up to 50% deoxyribonucleotides, and up to 58% 2'-O-methylnucleotides. Aurup et al (1992) describe methods for using T7 polymerase to produce transcripts containing 2'-fluoro-2'-deoxyuridine, 2'-fluoro-2'-deoxycytidine, and 2'-amino-2'deoxyuridine. (Aurup, 1992; Conrad, 1995; Ruffner, 1990). Further methods will be discussed below.

Nucleotides represented in the compounds above comprise a sugar, base, and a monophosphate group or a phosphodiester linkage. Accordingly, nucleotide derivatives or modifications may be made at the level of the sugar, base, monophosphate groupings or phosphodiester linkages. It is preferred that the nucleotides in the compounds above be ribonucleotides or RNA/DNA hybrids, however, other substitutions or modifications in the nucleotide are possible providing that endonuclease activity is not lost.

In one aspect of this invention, the sugar of the nucleotide may be a ribose or a deoxyribose such that the nucleotide is either a ribonucleotide or a deoxyribonucleotide, respectively. Furthermore, the sugar moiety of the nucleotide may be modified according to well known methods in the art [See for example: Saenger, 1984; Sober, 1970]. This invention embraces various modifications to the sugar moiety of nucleotides as long as such modifications do not abolish cleavage activity of the ribozyme. Examples of modified sugars include replacement of secondary hydroxyl groups with halogen, amino or azido groups; 2'-alkylation; conformational variants such as the O2'-hydroxyl being cis-oriented to the glycosyl $C_1$'-N link to provide arabinonucleosides, and conformational isomers at carbon $C_1$' to give alpha-nucleosides, and the like. Ring nitrogens may be replaced with carbon such as in 7 deazaguanosine, and z deazadenosine. In addition, the invention is directed to compounds with a substituted 2' hydroxyl such as 2' O-allyl, or 2' O-methyl. Alternatively, the carbon backbone of the sugar may be substituted such as in 2' C-allyl.

Accordingly, the base of the nucleotide may be adenine, 2-amino adenine, cytosine, guanine, hypoxanthine, inosine, methyl cytosine, thymine, xanthine, uracil, or another modified base (see below).

Nucleotide bases, deoxynucleotide bases, and ribonucleotide bases are well known in the art and are described, for example in Principles of Nucleic Acid Structure [Saenger, 1984]. Furthermore, nucleotide, ribonucleotide, and deoxyribonucleotide derivatives, substitutions and/or modifications are well known in the art [See for example: Saenger, 1984; Sober, 1970], and these may be incorporated in the ribozyme made with the proviso that endonuclease activity of the ribozyme is not lost. As mentioned previously, endoribonuclease activity may be readily and routinely assessed.

In addition, a large number of modified bases are found in nature, and a wide range of modified bases have been synthetically produced [See for example: Saenger, 1984; Sober, 1970]. For example, amino groups and ring nitrogens may be alkylated, such as alkylation of ring nitroaen atoms or carbon atoms such as $N_1$ and $N_7$ of guanine$_5$ and C of cytosine; substitution of keto by thioketo groups; saturation of carbon-carbon double bonds, and introduction of a C-glycosyl link in pseudour-dine. Examples of thioketo derivatives are 6-mercaptopurine and 6-mercaptcguanine. Bases may be substituted with various groups, such as halogen, hydroxy, amine, alkyl, azido, nitro, phenyl and the like. The phosphate moiety of nucleotide or the phosphodiester linkage of oligonucleotide is also subject to derivatization or modifications, which are well known in the art. For example, replacement of oxygen with nitrogen, sulphur or carbon gives phosphoramidates, (phosphorothioates, phosphorodithioates) and phosphonates, respectively. Substitutions of oxygen with nitrogen, sulphur or carbon derivatives may be made in bridging or non-bridging positions. it has been well established from work involving antisense oligonucleotides [Uhlmann, 1990] that phosphodiester and phosphorothioate derivatives may efficiently enter cells (Particularly when of short length), possibly due to association with a cellular receptor. Methylphosphonates are probably readily taken up by cells by virtue of their electrical neutrality.

A further aspect of the invention provides alternative linkages such as an amide, a sulfonamide, a hydroxylamine, a formacetal, a 3'-thioformacetal, a sulfide, or an ethylene glycol function to replace the conventional phosphodiester linkage. These modifications may increase resistance to cellular nucleases and/or improved pharmacokinetics.

Non-Exclusive List of Possibe Nucleotide Modifications

Sugar Modifications may be 2' fluoro, 2' amino, 2' O-allyl, 2' C-allyl, 2' O-methyl, 2' O-alkyl, 4'-thio-ribose, α-anomer, arabinose, other sugars, or non-circular analogues.

Phosphate Modifications may be phosphorothioate (non-bridging), phosphorodithioatre (non-bridging), 3' bridging phosphorothioate, 5' bridging phosphorothioate, phosphoramidates (including substituted phosphoramidates), 3' bridging phosphoramidate, 5' bridging phosphoramidate, methyl phosphonate, other alkyl phosphonates or phosphate triesters.

The phosphodiester linkage may be replaced by an amide, carbamate, thiocarbamate, urea, amine, hydroxylamine, formacetal, thioformacetal, allyl ether, allyl, ether, thioether, or PNA (peptide nucleic acid) linkage.

Modifications in base may be purine, 2,6-diaminopurine, 2-aminopurine, $O^6$-methylauanosine, 5-alkenylpyrimidines, 5-propyne pyrimidines, inosine, 5-methylcytosine, pseudouridine. Polymers of monophosphate alkanediols, or other alkanedlols.

Some nucleotides may be replaced with the following linkers: 1,3-propanediol, other alkanediols, or various polymers of ethyleneglycol (e.g. tetraethyleneglycol or hexaethyleneglycol) or abasic ribose or deoxyribose.

Other Modifications: The 3' or 5' end may be selected from: 3'—3' inverted linkage (inverted diester or inverted phosphoramidate). 3'—3' linked abasic ribose or deoxyribose or end capped e.g. G-cap, alkyl groups, cholesterol, or any other group which will block the activity of exonucleases.

Synthesis of Monomers Modified in the Sugar, Phosphate of Base

Modified sugars may be synthesized as follows: 2'-deoxy-2'-fluoro uridine (Sinha, 1984); 2'-deoxy-2' fluoro cytidine (Sinha, 1984); 2'-deoxy-2' fluoro adenosine; synthesis and incorporation into ribozyme (Olsen, 1991); 2'-deoxy-2'-amino uridine and 2'-deoxy-2'-amino cytidine (Heidenreich, 1994); 2'-O-allyl-(uridine or cytidine or adenosine or guanosine) (Available from Boehringer Mannheim, Manheim, Germany). 2'-deoxy-2'-C-allyl-ribonucleotides (Beigelman et al. 1995B); 2'-O-methyl ribonucleotides see review: (Sproat, B. S., 1991A) (also Available from Chemgenes, Waltham, Mass. or Glen Research, Sterling, Va. other 2'-O-alkyl-ribonucleotides, synthesis see (Monia, B. P., 1993; Sproat, B. S., 1991B); α-anomer of uridine, cytidine, adenosine and guanosine, see (Debart, F., 1992 and references therein); other modified sugars, etc. arabinose (Garbesi, A., 1993); hexose-thymidine (Augustyns, K., 1992) and linear substitutes for sugars.

Modified phosphates may be synthesized as follows: Phosphorothioate; synthesized by modification of oxidation procedure during phosphoramidite synthesis. Reagents commercially available from Perkin Elmer and others, products are mixture of isomers, some methods available for stereospecific synthesis of phosphorothioate, see: (Stec, 1991; Stec, 1995) phosphorodithioate; (Eldrup, A. B., 1994; Caruthers, 1991; Beaton, 1991); 3'-bridging phosphorothioate; 5' bridging phosphorothioate; phosphoramidates (nonbridging); (Froehier, B., 1988; Jager, A., 1988; Letsinger, R. L., 1988); 3' bridging phosphoramidate (NH replaces 3' O) (Letsinger, 1992; Gryaznov, S. M., 1995; Chen, J. K., 1995); 5' bridging phosphoramridate (NH replaces 5' O) (Gryaznov, S. M., 1992); metrhylphosphonate (reagents are commercially available; Glen Research or Chemgenes; Savchenko, 1994; Miller, 1991); 5'-deoxy, 5'-methylphosphonate (Szabo, 1995); other alkyl-phosphonates (Fathi, 1994A; Fathi, 1994B); phosphate triesters(Summers, 1986).

Replacements for the Phosphodiester Linkage may be synthesized as follows:

For review see (De Mesmaker, 1995); amides (Chur, 1993; Blommers, 1994; De Mesmaeker, 1993; De Mesmaeker, 1994A; De Mesmaeker, 1994B; Lebreton, 1993; Lebreton, 1994A; Lebreton, 1994B; Idsiak, 1993); carbamate (Waldner, 1994; Stirchak, 1987; Habus, 1994; thiocarbamate (Waldner,1995); ureas (Waldner, 1994); amines (De Mesmaeker,1994C; Caulfield, 1994); hydroxylamine (Debart, 1992; Vasseur, 1992); formacetal (Matteucci, 1990; Jones, 1993); thioformacetal (Jones, 1993); allyl ether (Cao,1994) ; allyl, ether, thioether (Cao, 1994); alkane (De Mesmaeker,1994; PNA (Nielsen, 1993A; Hanvey, 1992; Egholm, 1993; Nielsen, 1993B); PNA Synthesis (Egholm, 1992A; Egholm, 1992B); preparation of purine PNA monomers and oligos (available commercially from Millipore corporation).

Modified bases may be synthesized as follows: purine; synthesis and incorporation into ribozyme (Slim, 1992; Fu,1992; Fu, 1993); 7-deazaguanosine, synthesis and incorporation into ribozyme (Fu, 1993); inosine, synthesis and incorporation into ribozyme (Slim,1992; Fu, 1993)7-deazaadenosine, synthesis and incorporation into ribozyme (Fu, 1992; Seela, 1993). O6-methylguanosine, synthesis and incorporation into ribozyme (Grasby, 1993); 2,6-diaminopurine, synthesis (Sproat, 1991); 2-aminopurine, synthesis and incorporation into ribozyme (Ng, 1994; Tuschl, 1993); isoguanosine, synthesis and incorporation into ribozyme (Ng, 1994; Tuschl, 1993); xanthosine, synthesis and incorporation into ribozyme (Tuschl, 1993); 6-azathymidine, 6-aza-2'-deoxycytidine, synthesis and incorporation into oligonucleotides (Sanghvi, 1993); 5-alkenylpyrimidines; 5-propyne (Fenster et al. 1994); inosine (Chemgenes); 5-methylcytosine; pseudouridine; abasic ribose or deoxyribose (Beigelman et al. 1995A).

Detailed Listing of Nucleotide-Modifications Which Have Been Tested in Ribozymes Sugars Modifications may be made to the 2'OH group of the sugar at all non-conserved nucleotides; modifications tested have been 2'H (DNA), 2'F, 2'amino, 2'-O-allyl, 2'-O-methyl, 2'-C-allyl.

Selected modifications may be made to the 2'OH groups of the conserved nucleotides C3, U4, A6, N7, A9, G12, A13, A14, N15.2.

Modifications cannot be made to the 2'OH groups of G5, G8 and A15.1.(See FIG. 1)

For a ribozyme with good cleavage activity, modifications should not be made to G5, A6, G8, G12, A15.1 (except G12 can be 2'H (DNA)).

Generally, except for modifications at G5, G8 and A15.1, no single modification causes a big reduction in cleavage activity; however, activity decreases as more modifications are included in the ribozyme.

Phosphates

The phosphate groups of the non-conserved nucleotides may be phosphorothioates (phosphorothioated DNA or RNA). Preferably, when non-conserved nucleotides are DNA, only two or three phosphates at the 3' and 5' ends of the ribozyme are phosphorothioates. The phosphates 5' to the conserved nucleotides C3, U4, G5, G8 and G12, and 3' to A9 and N15.2, may be phosphorothioates; but phosphates 5' to A9, A13 and A14 may not be phosphorothioates.

Conserved nucleotides. (See FIG. 1 for Numbering)

C3

Sugar—2'-OH group can be modified (except, probably, for 2'amino). 2'H (Yang, 1992), 2'F (Pieken, 1991; Heidenreich, ;1992), 2'-O-allyl (Paolella, 1992), 2'-O-Methyl (Usman, 1995) are all modifications that permit cleavage.

Possibly cannot have 2'amino modification (several Cs in ribozyme had 2'amino modification which resulted in reduction in activity, and effect is probably due to 2'amino on C3 and/or C15.2) (Pieken, 1991).

Phosphate—5' phosphate can be phosphorothioate (Shimayama, 1993).

U4

Sugar—2'OH group can be modified. 2'H Yang, 1992), 2'F (Pieken, 1991; Heidenreich, 1992), 2'amino (Pieken, 1991), 2'-C-allyl (Usman, 1995), 2'-O-allyl (but keep as 2'OH if A6 is 2'-O-allyl) (Paolella, 1992) are modifications that permit cleavage.

Phosphate—5' phosphate can be phosphorothioate (Shimayama, 93).

G5

Base—2-amino group on G base is essential (cannot be inosine) (Odai, 1990; Fu, 1992).

Sugar—cannot make modifications to 2'OH of G5. Cannot have 2'H (Perreault, 1990; Perreault, 1991; Fu, 1992; Williams, 1992) 2'amino (Pieken, 1991; Williams, 1992), 2'-O-methyl (Paolella, 92), 2'F (Williams, 1992).

A6

Base—can be purine (i.e. 6-amino group is not essential) (Fu, 92). N7 cannot be C7 in A base (Fu, 1992).

Sugar—2' OH group can be modified. 2'H (Perreault, 1990; Olsen, 1991; Yang, 1992; Fu, 1992), 2'F (Olsen, 1991), 2'-O-allyl (but only if U4 is 2'OH) (Paolella, 1992) are modifications that permit cleavage.

N7

Seems to be a sensitive site for pyrimidine endonucleases; protection achieved if rN is rG or rA (Shimayama, 1993).

Sugar—2'OH group can be modified. 2'H (tested dT) (Yang, 1992), 2'F (Pieken, 1991; Heidenreich, 1992)

2'-amino (Pieken, 1991), 2'-O-allyl (Paolella, 1992), 2'-O-Methyl (Usman, 1995) are all modifications that permit cleavage.

3' phosphate can be phosphorcthioate (has been tested for N=U) (Shimayama, 1993).

G8

Sugar—cannot make modifications to 2'OH of G8. Cannot have 2'H (Fu, 1992; Williams, 1992; Yang, 1992), 2'F (Williams, 1992), 2'amino (Williams, 1992), 2'-O-allyl (Paolella, 1992). (Perreault 1991) observes may be 2'H, but Yang (1992) state this site is critical if many other conserved nucleotides are DNA.)

Phosphate—5' phosphate probably can be phosphorothioate (see N7 phosphate).

A9

Sugar—2'OH group can be modified. 2'H (Olsen, 1991; Fu, 1992; but Perreault (1991) says cannot be 2'H), 2'F (Olsen, 1991; Pieken, 1991), 2'-O-allyl (Paolella, 1992), 2'-O-Methyl (Usman, 1995) are all modifications that permit cleavage.

Phosphate—5' phosphate cannot be phosphorothioate (Buzayan, 1990; Ruffner, 1990). 3' phosphate can be phosphorothioate (Shimayama, 1993).

G12

Base—2-amino group is essential (cannot be inosine) (Slim, 1992).

Sugar—2'OH group can tolerate some modifications. 2'H (Perreault, 1991; Yang, 1992; Williams, 1992), 2'amino (Pieken, 1991; Williams, 1992) are OK. Cannot be 2'F (Williams, 1992), 2'-O-allyl (Paolella, 1992).

Phosphate—5' phosphate can be phosphorothioate (Shimayama, 1993).

A13

Base—Can change N7 to carbon in the adenine base (Fu, 1992). 6-amino group essential (cannot be purine) (Slim, 1992).

Sugar—2'OH group can tolerate some modifications. 2'H (Perreault, 1991; Yang, 1992), 2'-O-allyl (Paolella, 1992), 2'-O-Methyl (Usman, 1995) are modifications that permit cleavage. Cannot have 2'F if each of A13, A14, A15.1 have 2'F (Pieken, 1991).

Phosphate—5' phosphate cannot be phosphorothioate (Ruffner, 1990).

A14

Base—Can change N7 to carbon (Fu, 1992). Can be purine (Slim, 1992).

Sugar—2'OH group can tolerate some modifications. 2'H (Perreault, 1991; Yang, 1992), 2'-O-allyl (Paolella, 1992), 2'-O-Methyl (Usman, 1995) are modifications that permit cleavage. Cannot have 2'F if each of A13, A14, A15.1 have 2'F (Pieken, 1991).

Phosphate—5' phosphate cannot be phosphorothioate (Ruffner, 1990).

A15.1

Base—Can change N7 to C. (Fu, 1992). 6-amino group essential (cannot be purine) (Slim, 1992).

Sugar—Cannot modify 2'OH. Cannot have 2'H (Yang, 1992), 2'-O-allyl (Paolella, 1992), 2'F (if A13 and A14 also are 2'F) (Pieken, 1991).

N15.2

Sugar—selected modifications permit cleavage. 2'F (Pieken, 1991; Heidenreich, 1992), 2'-O-allyl (Paolella, 1992), 2'-O-Methyl (Usman, 1995) are modifications that permit cleavage.

Rates are low if 2'H (Yang, 1992). Possibly cannot have 2'amino modification (several cytosines in ribozyme had 2'amino modification which resulted in reduction in activity, and effect is probably due to C3 and/or C15.2) (Pieken, 1991). 3' phosphate can be phosphorothioate (Shimayama, 1993).

Modifications at the 3' end of an oligonucleotide or ribozyme

3'MEA (methoxyethylamine)phosphoramidate in last two (or last) internucleotide linkages; 3'—3' inverted diester linkage or 3'—3' inverted phosphoramidate (Shaw, 1991).

3'—3' inverted thymidine, or 3'—3' linked abasic ribose (Usman, 1995).

Any combination of the above listed nucleotide modifications, substitutions, or derivatizations, made at the level of the sugar, base, or monophosphate groups or phosphodiester linkages may be made in the compounds provided that endonuclease activity is not lost.

In addition, the compounds of the present invention may be prepared by methods known per se in the art for the synthesis of RNA molecules. (For example, according to recommended protocols of Promega, Madison, Wis., USA). In particular, the ribozymes of the invention may be prepared from a corresponding DNA sequence (DNA which on transcription yields a ribozyme, and which may be synthesized according to methods known per se in the art for the synthesis of DNA) operably linked to an RNA polymerase promoter such as a promoter for T3 or T7 polymerase or SP6 RNA polymerase. The RNA may be subsequently modified or modified nucleotides may be directly incorporated. For delivery see for example "Targeting and Delivery of Genes and Antiviral Agents into Cells by the Adenovirus Penton," G. Nemerow et al., U.S. Ser. Nos. 08/046,159 and 08/015, 225. It may be desirable for the target and ribozyme to be sequestered in the same cellular compartment [Sullenger and Cech, 1993].

The compounds may be introduced into cells by electroporation, PEG, high velocity particle bombardment or lipofectants, or introduced into cells by way of micromanipulation techniques such as microinjection, such that the compound enters the host cell. The present invention also includes other means of transfer such as genetic bullets (e.g. DNA-coated tungsten particles, high-velocity micro projectile bombardment) and electroporation amongst others [Maliga, 1993; Bryant, 1992; or Shimamoto, 1989].

The compounds of the present invention have extensive therapeutic and biological applications. For example, disease causing viruses in man and animals may be inactivated by administering to a subject infected with a virus, a compound in accordance with the present invention adapted to hybridize to and cleave specific RNA transcripts of the virus. Such compounds may be delivered by parenteral or other means of administration.

The compounds of the present invention have particular application to viral diseases caused for example, by the herpes simplex virus (HSV) or the human immunodeficiency virus (HIV-1, HIV-2). Further non-limiting examples of human and animal diseases which may be treated with the ribozymes of this invention include osoriasis, cervical preneoplasia, papilloma disease, bacterial and prokaryotic infection, viral infection. Examples include but are not limited to warts, dental caries, gingivitis, cytomegalovirus, hepatitis and neoplastic conditions, associated with the production of aberrant RNAs such as occurs in chronic myeloid leukemia, malignant melanoma or bladder carcinoma pancreatic cancer, acute lymphoblastic leukemia (ALL), restenosis and acute promyelocytic leukemia (APML or APL) and any disease involving altered patterns of gene expression or that involves the expression of genes that lead to abnormal or deleterious RNAs and/or proteins.

The period of treatment would depend on the particular disease being treated and could be readily determined by a physician. Generally treatment would continue until the disease being treated was ameliorated.

The ribozymes of the present invention also have particular application to the inactivation of RNA transcripts in bacteria and other prokaryotic cells, animals and yeast cells.

Methods for the introduction of RNA and DNA sequences into prokaryotic and eukaryotic cells are well known in the art for example as discussed by Cotten and Friedman [Cotten, 1990; Friedman, 1989]. The same widely known methods may be utilized in the present invention.

The compounds of this invention may be incorporated into cells by direct cellular uptake, where the ribozymes of this invention would cross the cell membrane or cell wall from the extracellular environment. Agents may be employed to enhance cellular uptake, such as liposomes or lipophilic vehicles, cell permeability agents, such as dimethylsulfoxide, and the like. The delivery/targeting molecule may be for example: RNA; modified RNA; DNA; modified DNA; peptides; peptide mimetics; steroids, cholesterol and derivatives; other steroids; fats (saturated and partially unsaturated); vitamins or mimetics e.g. biotin; folic acid; retnoic acid; proteins e.g. ferritin, LDL, insulin or specific antibodies; sugars and oligosaccharides. The invention includes linkage to other agents such as avidin, biotin (Partridge et al. 1991, 1993), poly-(L-lysine) (Bunnell, 1992), cholesterol or thiocholesterol (Bouterin, 1989; Letsinger, 1989; Oberhauser, 1992), phospholipids (Shea, 1990), long chain diols (Kabanov, 1990), neoglycoproteins, glycoproteins (Bonfils, 1992), protein A, antibodies (Leonetti, 1990), cationic lipids, lipofectamine, lipofectin (COTMA, DOTMA, DOTAP)(Bennett, 1992), targeted liposomes (Leonetti, 1990; Loke, 1988; Stull et al. 1995).

The compounds of the present invention may be combined with pharmaceutically and veterinarally acceptable carriers and excipients which are well known in the art, and include carriers such as water, saline, dextrose and various sugar solutions, fatty acids, liposomes, oils, skin penetrating agents, gel forming agents and the like, as described for example in Remington's Pharmaceutical Sciences, 17th Edition, Mack Publishing Co., Easton, Pa., Edited by Ostol et al., which is incorporated herein by reference.

The compounds of this invention may be provided in a composition with one or more anti-viral, anti-fungal, anti-bacterial, anti-parasitic, anti-protazoan or antihelminthic agents or the like, for example as described in the Merck Index (1989) 11th Edition, Merck & Co. Inc.

Therapeutic composition may involve topical application of ribozyme to the size of disease. For example, in the treatment of Herpes virus lesions, ribozymes may be formulated into a cream containing a concentration of 0.1 nM to 100 mM ribozyme, preferably 1 nM to 1 mM. The cream may then be applied to the site of infection over a 1 to 14 day period in order to cause amelioration of symptoms of the infection. Prior to the final development of topical formulations for the treatment of virus infection, effectiveness and toxicity of the ribozymes and formulations involving them may, for example, be tested on an animal model, such as scarified mouse ear, to which virus particles, such as $2 \times 10^6$ plaque forming units are added. A titer of infectious virus particles in the ear after treatment can then be determined to investigate effectiveness of treatment, amount of ribozyme required and like considerations. Similar investigations in animal models prior to human trials may also be conducted, for example, in respect of the treatment of psoriasis, papilloma disease, cervical preneoplasia, and in diseases such as HIV infection, bacterial or prokaryotic infection, viral infection and various neoplastic conditions, which involve a deleterious RNA species.

Compositions for topical application are generally in the form of creams, where the ribozymes of this invention may be mixed with viscous components. The compounds of this invention may be incorporated into liposomes or other barrier type preparations to shield the ribozymes from nuclease attack or other degradative agents (such as adverse environmental conditions such as UV light).

Compositions may be provided as unit dosages, such as capsules (for example gelatin capsules), tablets, suppositories and the like. Injectable compositions may be in the form of sterile solutions of ribozyme in saline, dextrose or other media which may be buffers or contain stabilizers, antioxidants or similar agents. Compositions for oral administration may be in the form of suspensions, solutions, syrups, capsules, tablets and the like. Ribozymes may also be provided in the form of an article for sustained release, impregnated bandages, patches and the like. The compounds of this invention may be embedded in liposomes or biodegradable polymers such as polylactic acid. Pharmaceutical compositions which may be used in this invention are described, for example, in Remington's Pharmaceutical Sciences, see above.

The compounds described herein may also be used as diagnostics. The compounds above may be designed to detect a particular genetic defect or as RNA restriction enzymes or for gene mapping. By running two reactions in parallel, one in contact with the catalytically active compound above one may be able to detect a genetic mutation, deletion or translocation. The method may be accompanied by an amplification step either the reaction or after the reaction with the catalytic compound. The amplification may be based upon polymerase chain reaction (PCR), Q-beta replicase (see Stefano, J. E. U.S. Pat. No. 5,472,840); ligase chain reaction (Kramer et al. WO 94/16105); reverse transcriptase PCR (RT-PCR), self sustained sequence replication (3SR)(SIBIA, Baxter Diagnostics); nucleic acid sequence based amplification (NASBA) (Cangene Corp), ligation activated transcription (LAT) Life Technologies Inc., Gaithersburg, Md.); ligase chain reaction (LCR) (OmniGene, Inc., Cambridge, Mass.; Abbott Labs, Abbott Park, Ill.; ApplIed Biosystems, Foster City, Calif.; Amgen, Thousand Oaks, Calif.; Beckman Research Institute); repair chain reaction (RCR) (ImClone Systems Inc. NY, N.Y.); and strand displacement activation (SDA) (Becton Dickenson Research Center, Research Triangle Park, N.C.). Other diagnostic methods maybe found in De La Monte et al. WO 94/23756; Bockman et al. WO 94/13833 or Lamond et al. EP 519,463. Alternatively, the methods may be coupled with a very sensitive technique such as an antibody/PCR type assay (Carter et al., 1992) Science 258; 120.

The present invention will now be illustrated by way of non-limiting Examples only, with reference to the following non-limiting Examples, and Figures.

Experimental

Nomenclature

The cleavage kinetics of a number of substrates by various hammerhead ribozymes were investigated. The sequences of the substrate molecules are taken from naturally occurring mRNAs and are identified by their origin. The GH series are derived from a sequence found in rat growth hormone mRNA, the TAT series are from the TAT mRNA of HIV-1 and the Kr series are derived from the mRNA of the Krüppel gene of *Drosophila melanogaster*.

The ribozymes and substrates with the prefix OU, are similar to, and in some cases identical to the well-characterized hammerhead entitled HH16 (Hertel et al., 1994; Hertel et al., 1996). The two series of substrates for the OU ribozymes are prefixed OU S, and OU CS. The OU S series contain a guanine ribonucleotide at the 13th position from the 5' end, complexed to the OU ribozymes this forms a G-U base pair. The OU CS (Complementary Substrate) series contains an adenine ribonucleotide in that position, thus forming a Watson-Crick A-U pair in complex with the OU ribozymes.

Ribozymes are denoted by an R following the identifying prefix, and substrates by the letter S which are further identified by a number denoting their length in nucleotides, e.g. S13. There are two versions of hammerhead ribozyme used in this paper, and they are denoted as ribozymes A and B. Ribozymes A (RA) are composed solely of RNA (with the exception of the 3' nucleotide) whereas ribozymes B (RB) possess DNA in the arms that hybridise to the substrate, with the exception of nucleotides 15.1 and 15.2 which remain as RNA (FIG. 1). The numbering system of Hertel et al. (Hertel, et al. 1992) is used throughout. The number of nucleotides n he hybridising arms (for ribozymes) or on each side of $C_{17}$ (for substrates) is given as a suffix to the name with the first number referring the 5' side and the second to the 3' side. For example, Kr S17-10/6 is a 17 mer substrate with 10 nucleotides 5' of the $C_{17}$ and 6 nucleotides to the 3' side, and is the substate complementary to the ribozyme Kr RA-6/10 (FIG. 2).

Preparation of Oligonucleotides

Oligonucleotides were synthesized using an Applied Biosystems (Foster City, Calif.) model 391 DNA synthesizer. Oligonucleotides with the prefix OU were prepared using reagents obtained from Perkin Elmer Applied Biosystems Division, Foster City, Calif.). Protected DNA phosphoramidite monomers were from Millipore (Bedford, Mass.) or Auspep (Melbourne, Australia). RNA monomers, protected at the 2'-hydroxyl with tert-butyldimethylsilyl groups (tBDMS), were from the same sources. For convenience in the syntheses, all the oligonucleotides have a deoxyribonucleotide at their 3' end. Deprotection and purification of oligonucleotides were as described previously (McCall, et al., 1992), with the exception that the removal of the t-BDMS group from the 2' position was achieved with the use of neat triethylamine trihydrofluoride for 24 hours at room temperature, followed by precipitation of the oligonucleotide with 10 volumes of 1-butanol prior to gel purification. The purity of each oligonucleotide was checked by labeling its 5'-end with $^{32}$P phosphate using T4 polynucleotide kinase (New England Biolabs, Beverly, Mass. USA) and γ-$^{32}$P ATP (Bresatec, Adelaide, S.A., Australia), electrophoresing the molecules on a 10 or 15% polyacrylamide gel containing 7M urea, and visualizing the molecules by autoradiography or using a Molecular Dynamics PhosphorImaging system (Sunnyvale, Calif.) ; all oligonucleotides were at least 98% pure as judged by this assay. The concentrations of the purified oligonucleotides were determined by UV spectroscopy using the following molar extinction coefficients for the various nucleotides at 260 nm: A, 15.4× $10^3$; G, 11.7×$10^3$; C, 7.3×$10^3$; T/U, 8.8×$10^3$ Lmol$^{-1}$cm$^{-1}$. All oligonucleotides were stored in distilled, deionized and autoclaved water at −20° C.

Oligonucleotide Sequences

The oligonucleotides used in this study are as follows. Capital letters refer to ribonucleotides, lower-case letters refer to deoxyribonucleotides.

Growth Hormone System (GH). GH RA-10/10, 5' GACACCUUCAU CUGAUGA GUCC UUUU GGAC GAAAC CCGCAGGt 3'; GH RB-10/10, 5' gacacttcat CUGAUGA GUCC UUUU GGAC GAAAC ccgcaggt 3'; GH S13-6/6, 5' GCGGGUCAUGAAg 3'; GH S21-10/10, 5' ACCUGCGGGUCAUGAAGUGUc 3'. (SEQ ID NOS 1–4)

Krüapel System (Kr). Kr RA-10/10, 5' CUCCAGUGUG CUGAUGA GUCC UUUU GGAC GAAAC UCGCAAAt 3'; Kr RB-10/10, 5' ctccagtgtg CUGAUGA GUCC UUUU GGAC GAAAC tcgcaaat 3'; Kr RA-6/10, 5' AGUGUG CUGAUGA GUCC UUUU GGAC GAAAC UCGCAAAt 3'; Kr S21-10/10, 5' AUU UGC GAG UCC ACA CUG GAg 3'; Kr S18-10/7; 5' AUU UGC GAG UCC ACA CUg 3'; Kr S17-10/6; 5' AUU UGC GAG UCC ACA Ct 3'; Kr S16-10/5, 5' AUU UGC GAG UCC ACA c 3'; Kr S15-10/4, 5' AUU UGC GAG UCC ACa 3'; Kr S14-10/3, 5' AUU UGC GAG UCC Ac 3'; Kr S13-6/6, 5' GCGAGUCCACACt 3'; Kr S16-5/10, C GAG UCC ACA CUG GAg 3'. (SEQ ID NOS 5–15), respectively.

TAT System (TAT). TAT RA-10/10, 5' GUCCUAGGCU CUGAUGA GUCC UUUU GGAC GAAAC UUCCUGGa 3'; TAT RA-6/6, 5' UAGGCU CUGAUGA GUCC UUTU GGAC GAAAC UUCc 3; TAT RB-10/10, 5' gtcctaggct CUGAUGA GUCC UUUU GGAC GAAAC ttcctgga 3'; TAT RA-10/5, 5' GUCCUAGGCU CUGAUGA GUCC UUUU GGAC GAAAC UUc 3; TAT RA-5/10, 5' AGGCU CUGAUGA GUCC UUUU GGAC GAAAC UUCCUGGa 3'; TAT S13-6/6, 5' GGAAGUCAGCCUa 3', TAT S21-10/10, 5' TCC AGG AAG UCA GCC UAG GAc 3'; TAT S16-10/5, 5' TCC AGG AAG UCA GCC t 3'; TAT S16-5/10, 5' G AAG UCA GCC UAG GAc 3'; TAT S14-10/3, 5' TCC AGG AAG UCA GC 3'; TAT S15-10/4, 5' TCC AGG AAG UCA GCc 3'; TAT S17-10/6, 5' TCC AGG AAG UCA GCC Ua; TAT S18-10/7, 5' TCC AGG AAG UCA GCC UAg 3'; TAT S19-10/8, 5' TCC AGG AAG UCA GCC UAG g 3'. (SEQ ID NOS 16–29).

OU System OU RA-8/8, 5' GCG AUG AC CUGAUGA GGCC GAAA GGCC GAAAC GUU CCC dT 3' (SEQ ID NO. 30); OU RA-6/8, 5' G AUG AC CUGAUGA GGCC GAAA GGCC GAAAC GUU CCC dT 3' (SEQ ID NO. 31); OU S-13-8/4, 5' GCG AAC GUC dG 3' (SEQ ID NO: 32); OU S-14-8/5, 5' GGG AAC GUC GUC G dT 3' (SEQ ID NO: 33); OU S-15-8/6, 5' GGG AAC GUC GUC GU dC 3' (SEQ ID NO. 34); OU S-16-8/7, 5' GGG AAC GUC GUC GUC dG 3' (SEQ ID NO. 35); OU S-18-8/8, 5' GGG AAC GUC GUC GUC GC dC 3' (SEQ ID NO. 36); OU CS-13-8/4, 5' GGG AAC GUC GUC dA 3' (SEQ ID NO. 37); OU CS-14-8/5, 5' GGG AAC GUC GUC A dT 3' (SEQ ID NO. 38); OU CS-15-8/6, 5' GGG AAC GUC GUC AU dC 3' (SEQ ID NO. 39); OU CS-16-8/7, 5' GGG AAC CUC GUC AUC dG 3' (SEQ ID NO. 40); OU CS-18-8/8, 5' GGG AAC GUC GUC AUC GC dC 3' (SEQ ID NO. 40).

Kinetic Experiments

Ribozyme Excess Experiments

Unless otherwise stated, the kinetic experiments were performed at 37° C. with ribozyme and substrate (labeled at the 5' end with $^{32}$P-phosphate) in 10 mM MgCl$_2$ and 50 mM buffer (Tris or Mes), using the following procedure. The substrate concentrations were kept very high to ensure complete complex formation and were in the range 2–4 μM (typically 2 μM) and the ribozyme concentration was at least 1.5 times that of the substrate (typically 3 μM). The ribozyme and substrate together in buffer were pre-treated by heating to 85° C. for 2 minutes, centrifuging briefly, and then placing at the reaction temperature for a few minutes. The reaction was initiated by the addition of MgCl$_2$. Samples were removed at various time intervals and quenched by addition to two volumes of gel loading buffer containing 80% formamide and 20 mM EDTA. The fraction of substrate cleaved in each sample was determined by separation of the substrate from the 5'-product in a 15% polyacrylamide gel containing 7 M urea, and quantifying the amounts of each using a Molecular Dynamics PhosphorImaging system and imageQuant software (Molecular Dynamics, Sunnyvale Calif.). The kinetic parameters were obtained by fitting the data for percentage of product formed ($P^f$) at any given time (t) to the equation:

$$P_t = P_\infty - (\exp(-k_{obs}t)P_j)$$

where $P_t$ is the amount of product at time t, $P_\infty$ is the amount of product at t=0, $k_{obs}$ the first-order rate constant for the reaction and $P_j$ is the difference between the percentage of product at t=∞ (infinity) and t=0. This is a first-order kinetic equation from which $k_{obs}$, $P_\infty$ and $P_{j\Omega}$ are determined by least-squares fitting of the data. $P_\infty$ was around 0.7 to 0.8, i.e. about 70 to 80% of the substrate was cleaved at the end of the reaction. The observed rate constants, $k_{obs}$, presented in Table 1 are the mean±standard deviation of at least two independent experiments.

The experiments with the OU System were performed at 25° C. with ribozyme and substrate (labeled at the 5' end with $^{32}$P-phosphate) in 10 mM $MgCl_2$ and 50 mM buffer (Tris, pH 7.60 @ 25° C.). The substrate concentrations were 180 nM and the ribozyme concentration was 2.2 μM. The ribozyme and substrate together in buffer were pre-heated to 85° C. for 2 minutes, centrifuged briefly, and then placed at 25° C. for a few minutes. The reaction was initiated by the addition of $MgCl_2$. The separation of substrate from the cleavage products and kinetic analysis was performed as described previously.

Result

Long-Armed Ribozymes Cleave Short Substrates Faster Than Long Substrates

Ribozymes with 10 nucleotides in each hybridizing arm form complexes with symmetric 13-nucleotide substrates that contain 6 base pairs in each of helices I and III, while the same ribozymes form complexes with symmetric 21-nucleotide substrates that have 10 base pairs in each of the helices. With the exception of TAT RA-10/10 such ribozymes cleave 13-mer substrates significantly faster than the corresponding 21-mer substrates (Table 1). The reactivity of TAT RA-10/10 appears to be anomalous and is apparently modulated by some spurious base pairing (see discussion). Since short double-helices generally are less stable than longer double-helices, the relative cleavage rates of 13 versus 21-nucleotide substrates by 10/10 ribozymes are consistent with a cleavage mechanism that requires one or both of helices I and III to be relatively unstable.

Cleavage is Rapid With a Short Helix I

In order to elucidate which of the helices was required to be less stable a series of substrates were made which would form helices of different lengths with the symmetric (10/10) ribozymes. The cleavage rates of these substrates by their cognate ribozymes are shown in Table 2. With the exception of the anomalous TAT RA-10/10, ribozymes cleaved substrates which formed 5 base pairs in helix I (S16-10/5) with significantly greater rate constants than the substrates which formed 5 base pairs in helix III (S16-5/10). In each case the other helix consisted of 10 base pairs. In a control experiment, TAT S16-10/5 and TAT S16-5/10 were cleaved with similar efficiencies by the short-armed ribozyme TAT RA-6/6 ($ks_{obs}$=3.1 min$^{-1}$ and 3.8 min$^{-1}$ respectively at pH 7.13), demonstrating that there was no intrinsic difference in the cleavability of the two TAT substrates. Similar results are seen when the length of the helix is limited by the length of the hybridising arms of the ribozyme rather than the length of the substrates, for example, two asymmetric ribozymes, TAT RA-10/5 and TAT RA-5/10, were synthesised and their ability to cleave the symmetric 21-mer substrate TAT S21-10/10 was examined (Table 3). A substrate in a complex with a helix I of 5 base pairs as cleaved more efficiently than when in a complex with a helix I of 10 base pairs. These conclusions are confirmed by the observation that the ribozyme Kr RA-6/10 cleaved the substrate Kr S21-10/10 with a rate constant of 6.7 min$^{-1}$ at pH 7.13 (Table 3), more than 10-fold greater than the rate constant for the symmetric ribozyme Kr RA-10/10 at pH 8.0 (Table 1).

The Optimum Lengths of Helices I and III

Figure 3:
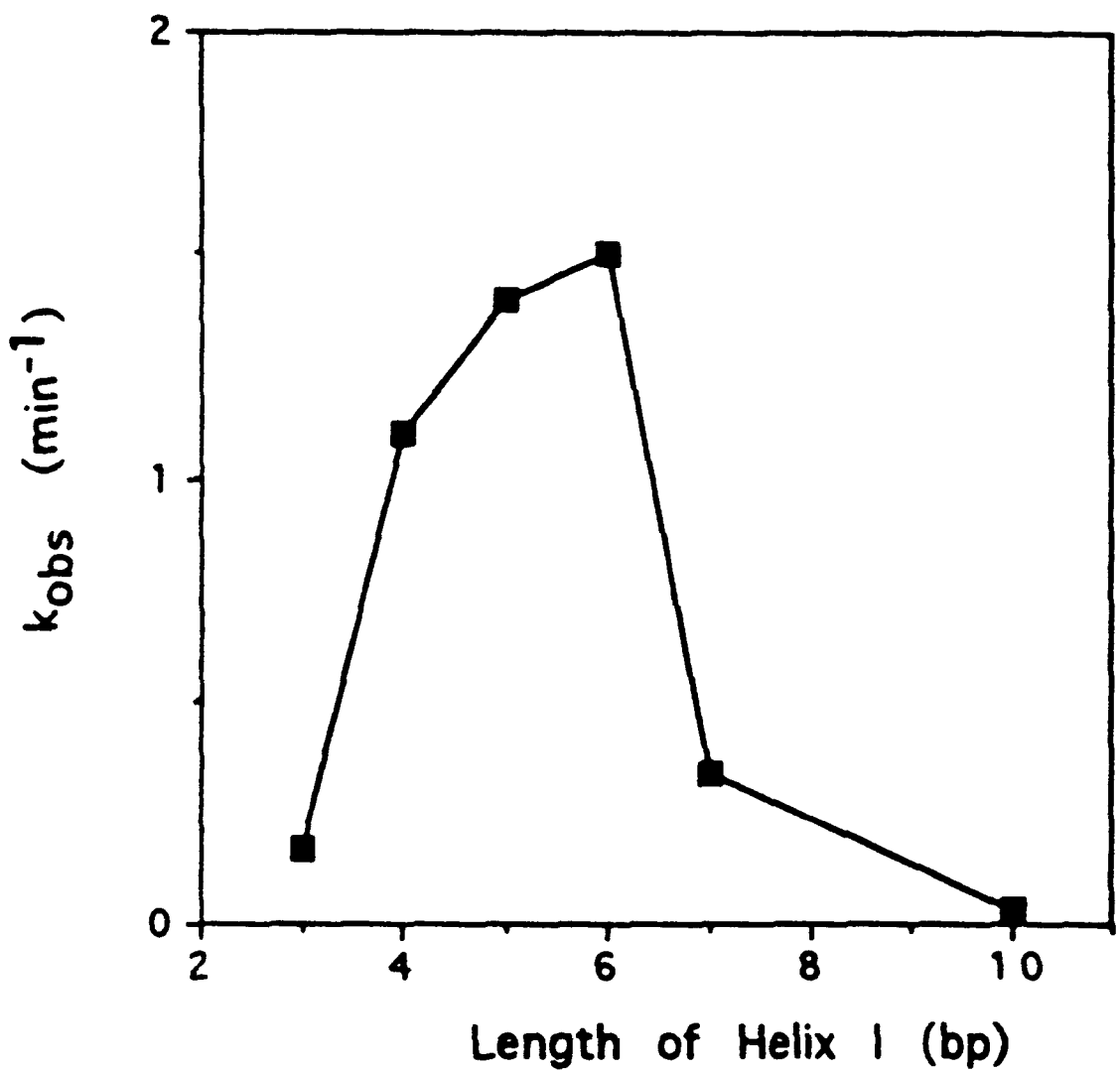
FIG. 3 Dependence of rate constants on length of helix I with helix III constant at 10 bp. Substrates with varying numbers of nucleotides to the 3' side of the cleavage site and 10 nucleotides on the 5' side are cleaved by their cognate ribozyme; ■ Kr RA-10/10; Reactions conditions; 10 mM $MgCl_2$, 37° C., pH 6.42.
Figure 4:
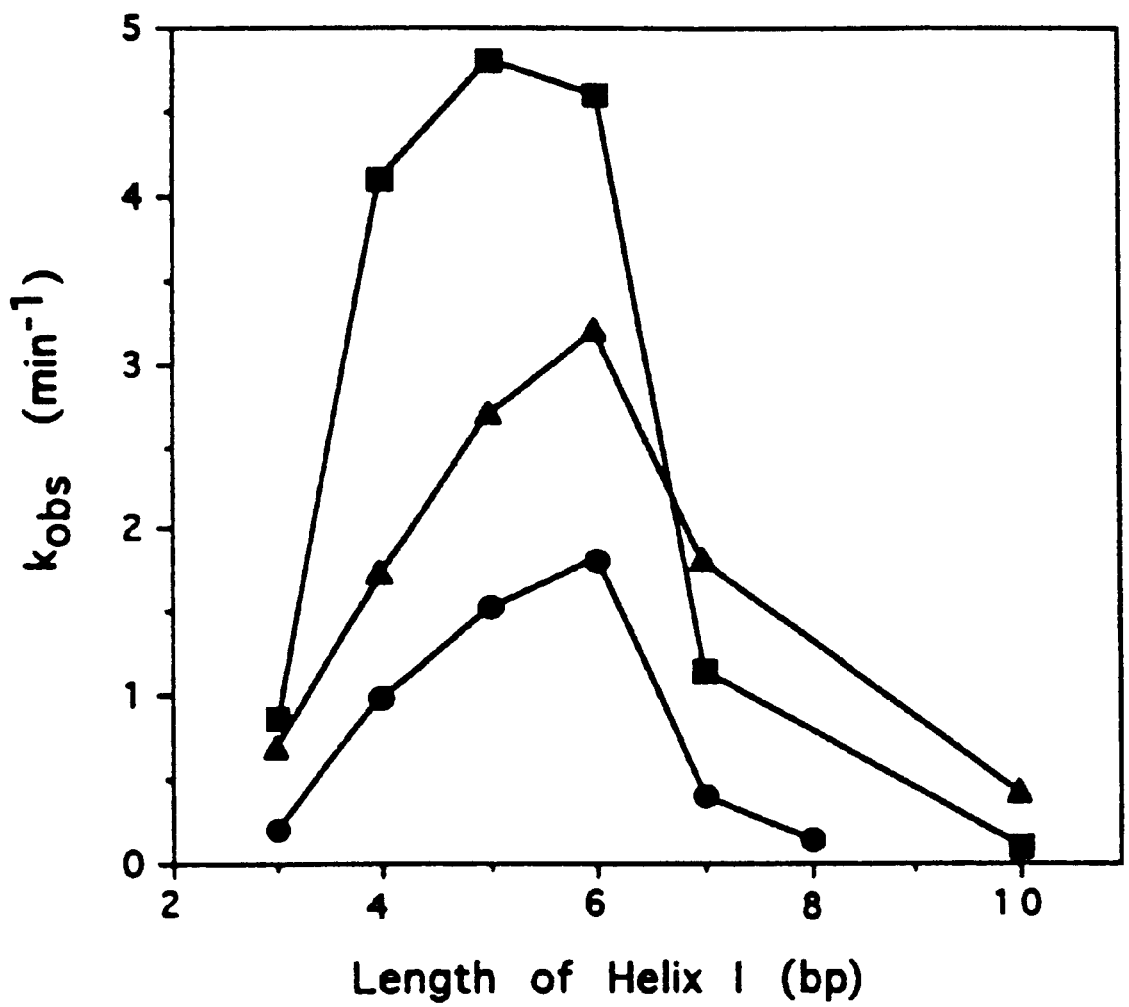
FIG. 4 Dependence of rate constants on length of helix I with helix III constant at 10 bp. Substrates with varying numbers of nucleotides to the 3' side of the cleavage site and 10 nucleotides on the 5' side are cleaved by their cognate ribozymes; ■ Kr RA-10/10; ▲ Kr RB-10/10; ● TAT RB-10/10. Reactions conditions; 10 mM $MgCl_2$, 37° C., pH 7.13.
Figure 5:
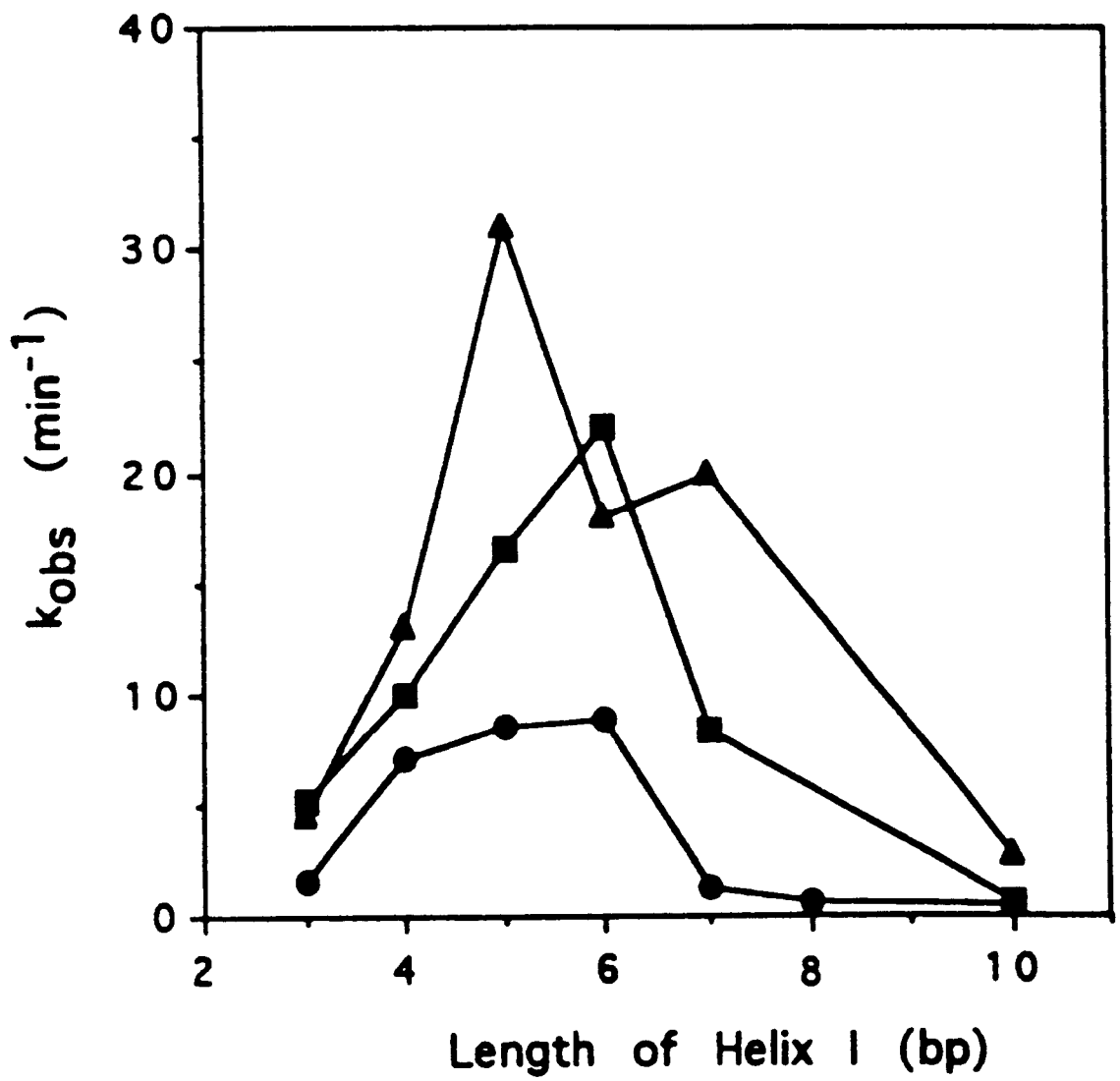
FIG. 5 Dependence of rate constants on length of helix I with helix III constant at 10 bp. Substrates with varying numbers of nucleotides to the 3' side of the cleavage site and 10 nucleotides on the 5' side are cleaved by their cognate ribozymes; ■ Kr RA-10/10; ▲ Kr RS-10/10; ● TAT RB-10/10. Reactions conditions; 10 mM $MgCl_2$, 37° C., pH 8.00.

To determine the optimum length of helix I, TAT and Kr substrates were prepared with varying numbers of nucleotides to the 3' side of the cleavage site, and a constant 10 nucleotides to the 5' side. Rate constants for cleavage of the substrates by TAT RB-10/10, Kr RA-10/10 and Kr RB-10/10 were measured at a number of pHs (FIGS. 3,4,5). These data show that, with a helix III of 10 base pairs, the optimum length of helix I is 5±1 base pairs. No significance is attached to the apparent double peak in activity for Kr RB-10/10 since the rate constants measured above approximately 15 min$^{-1}$ are very unreliable because of the difficulty associated with sampling the reaction at such short time intervals.

The optimum length for helix III has not been studied as extensively as for helix I. However, available data would indicate that the substrate which forms the complex with a 10 base-pair helix III is cleaved faster than that which forms a 6 base-pair helix III, when helix I has 6 base-pairs. Table 4 shows the rate constants for cleavage of substrates S17-10/6 and S13-6/6 by three ribozymes, TAT RB-10/10, Kr RA-10/10 and Kr RB-10/10, in which the ribozyme-substrate complexes have either 10 or 6 base pairs in helix III, while there is a constant 6 base pairs in helix I. However, the difference in rate constants is only two-fold at most. Thus, the effect of the length of helix !!I on cleavage rate constants is much less pronounced than the effect of the length of helix I.

Mismatch in the Substrate

Figure 7:
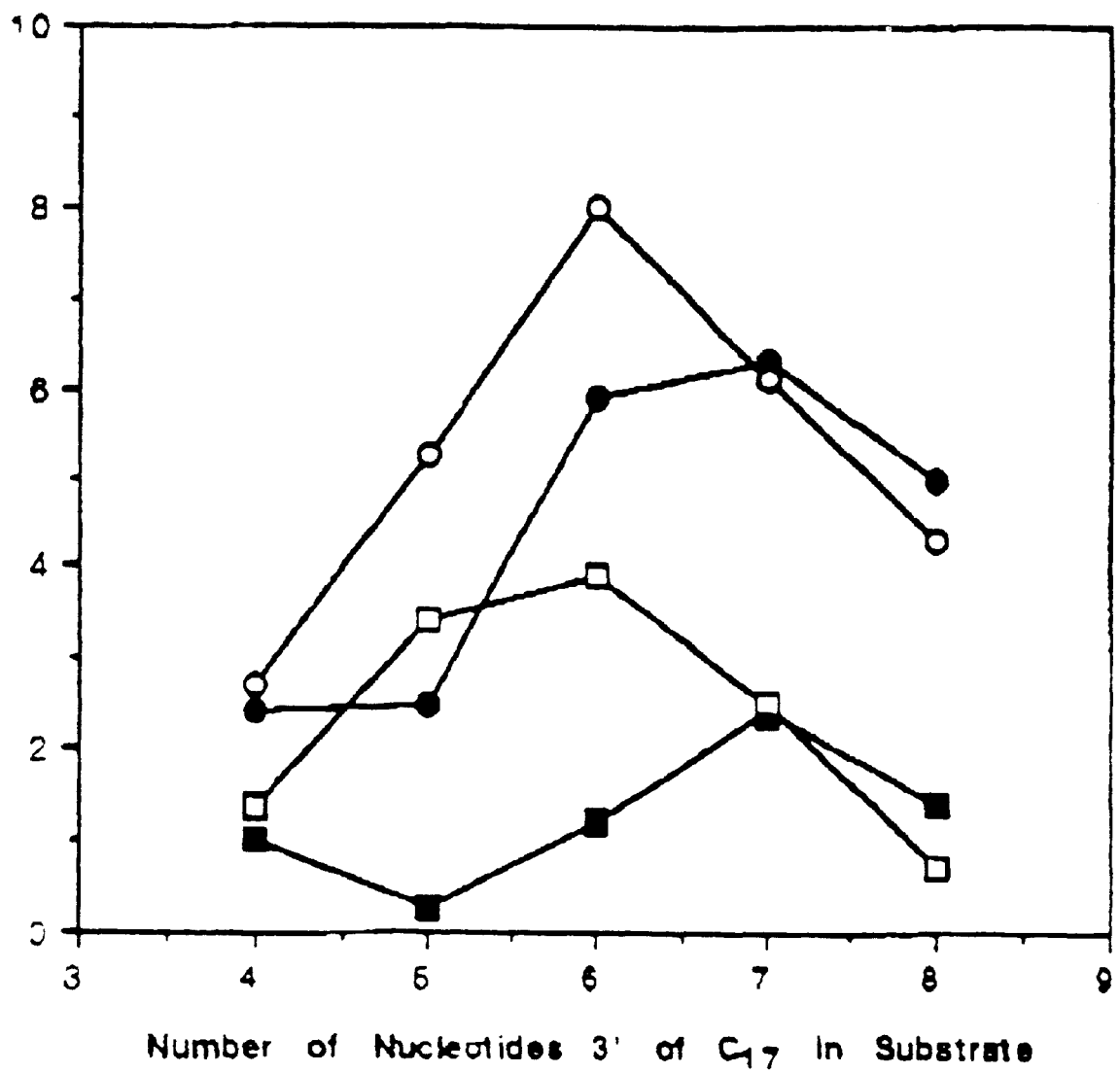
FIG. 7 Dependence of the rate constants on the number of nucleotides to the 3' side of $C_{17}$ in the substate. The following systems are shown: ■ OU RA-8/8+OU S; ◻ OU RA-8/8+OU CS; ● OU RA-6/8+OU S; ○ OU RA-6/8+OU CS. Reaction conditions: 10 mM $MgCl_2$, 25° C., pH 7.60.

The results in Table 5 and FIG. 7 clearly demonstrate that in the OU system, which has been previously extensively characterized (Hertel et al, 1994), optimum cleavage rates are achieved with a helix I length of 6 nucleotides.

The existence of the guanosine ribonucleotide at position 1.4 in the ribozyme substrate complex (Numbering according to Hertel et al., 1992) clearly inhibits the reactivity of the hammerhead for helix lengths of 6 nucleotides and shorter.

Discussion

Throughout this series of experiments ribozyme was in excess of substrate and high concentrations of pre-formed ribozyme and substrate complexes were used. Therefore neither association of the ribozyme and substrate nor the dissociation of the cleavage products from the ribozyme play any role in determining the observed cleavage rate constants. These results demonstrate for the first time that the cleavage step $k_2$ (Scheme 1) is significantly affected by the length of helix I.

The Conformational Flexibility of Helix I and the Stability of Helix III

These experiments are consistent with a model for the cleavage reaction in which a transient, partial or full dissociation of helix I allows an obligatory structural reorganisation of the conserved domain. With this model the requirement for helix I to be of a particular length and for the absence of a distinct optimum length for helix III can be explained. If helix I is too long, the process would be hindered by the slow dissociation of that helix; and if helix I is too short, the active complex may be too unstable. If helix III is too short, the probability that the entire substrate will dissociate upon the dissociation of helix I is quite high, resulting in a decrease in the overall rate constant for cleavage. This model of ribozyme cleavage is also able to account for the observation that substitution of DNA for RNA in the hybridising arms of the ribozyme (Hendry, et al. 1992; Shimayama, et al. 1993) or in portions of the substrate (Shimayama, 1994) apparently increases the rate constant for the cleavage step in some circumstances.

A number of publications demonstrate major changes in interhelical angles as measured by electrophoretic mobility and other methods in response to magnesium ion concentration (Bassi, et al. 1995; Amiri, et al. 1994; Gast, et al. 1994). Magnesium ions apparently induce the hammerhead to fold in to a conformation in which helix I subtends a small angle with helix II (Bassi, et al. 1995). Interestingly, in the presence of 2 mM $Ma^{2+}$ ions and only with a relatively stable helix III of 9 bp, helices I and II were found to move closer together (Amiri, et al. 1994; Gast, et al. 1994). It appears that the active form of the ribozyme has helices I and II in relatively close proximity. The magnesium ion induced flexibility in helix I seen in these studies may be related to the observations we have made here on the requirement for a degree of instability in helix I. There is however no evidence of strand dissociation in the movement of helix I seen in the electrophoretic studies.

Other studies are consistent with the notion that helix I needs to be relatively unstable and helix III needs to be more stable. In the context of a very long helix III, helix I was able to be reduced to as few as 3 base pairs without loss of activity (Tabler, et al. 1994); however, in that case, despite the fact hat the ribozyme and substrate were pre-annealed, the observed rate constants were only about 0.01 $min^{-1}$ at pH 8, 20 mM $MgCl_2$, which is about 1000-fold slower than would be expected for efficient cleavage of short substrates. Mismatches in either of helix I or III close to the conserved domain were shown to cause a dramatic decrease in activity, but mismatches more distal in helix I had only marginal effects (Zoumadakis, et al. 1994). In the context of relatively short substrate binding helices (Werner, et al. 1995), mismatches close to the core in helix I were tolerated much more than in helix III, where mismatches in any of the 4 inner-most base pairs caused a significant decrease in $k_2$. In the context of a hammerhead with very long helices I and II, it was observed that elongation of helix III from 3 to 9 base pairs caused a more than 100-fold increase in observed rate constant (Amiri, et al. 1994). In another study (Ellis, et al. 1993), cleavage of relatively long transcripts with excess ribozyme showed very significant decreases in activity when helix III was reduced from 8 to 4 effective base pairs, albeit under conditions where the cleavage event did not appear to be rate determining.

The molecular basis of he conformational chance cannot be deduced from the observations we have made here. The crystal structures of substrate analogue hammerhead ribozyme complexes (Pley, et al. 1994; Scott, et a:. 1995) show an inactive structure with the latent nucleophile not correctly positioned for in-line attack at the appropriate phosphate group. It is not clear how that inactive structure found in the solid state would convert into the active form, although several groups have speculated on how this might occur (Scott, et al. 1995; Setlik, et al. 1995).

Special Factors Restricting the Conformational Change Via Helix I

In the crystal structures (Pley, et al. 1994; Scott, et al. 1995) where the hammerhead ribozyme complexed with a substrate analogue, certain phosphate and sugar groups in the 5' arm of the ribozyme are close to phosphate groups in the distal part of helix II near loop II. Specifically, in the crystal structure by Pley et al. (Pley, et al. 1994), the interactions involve the 4th and 5th nucleotides in the 5' arm of the ribozyme (nucleotides 2.4 and 2.5) and two nucleotides in helix II (nucleotides 11.3 and 11.4); in the structure by Scott et al. (Scott, et al. 1995), the interactions are between nucleotide 2.5 and nucleotide 11.4. Since we have observed that optimum cleavage rates are observed when helix I is 5±1 base pairs in length, it may be that these inter-helix interactions might be an important factor in the cleavage mechanism. If this is the case, the optimum cleavage rates should always be observed with helix I of about 5 nucleotides irrespective of the strength of the interaction. This work is in progress.

The ribozyme TAT RA-10/10 appears to be a special case. This ribozyme displays anomalous activity in that it cleaves its 13-mer substrate TAT S13-6/6 more than 40 fold slower than does the shorter analogue TAT RA-6/6 at pH 8.00 (Hendry, et al. 1995). The source of the anomalous behaviour must lie in the terminal nucleotides of the 5' arm of the ribozyme since TAT RA-10/5 cleaves TAT S13-6/6 with a rate constant of only 0.09±0.01 $min^{-1}$ at pH 7.13, 50 fold slower the cleavage of that substrate by TAT RA-5/10 under the same conditions. In this context we note that the terminal nucleotides in the 5' arm of the ribozyme have the base sequence 5' GUCC, which is complementary to 4 bases in helix II, and in addition there is a high degree of complementarity between the sequences $A_{2.5}$ to $C_3$ and $G_3$ to $U_{L2.1}$. Thus, the anomalous cleavage rates of TAT RA-10/10 appear to be caused by spurious base pairing interactions.

The kinetics of HH16, have been extensively studied (Hertel et al., 1994), including a recent paper on the effect of shortening helix I (Hertel et al., 1996). The ribozyme is widely held to be an example of a well understood and well behaved hammerhead in which the cleavage step is rate-determining. Curiously, HH16 has a G-U mismatch at position 1.4–2.4 in the standard nomenclature. Uhlenbeck's data did not show the expected (from our point of view) peak in cleavage rate constant when helix I was around 5 or 6 nucleotides in length. We investigated this system further, synthesizing a system analogous of HH16, as well as a series of substrates, varying in length from 13 to 18 nucleotides, in which the mismatch at position 1.4–2.4 was replaced with a Watson-Crick A-U pair.

The cleavage rate constant for the hammerhead most resembling HH16, OU RA-8/8+OU S-18-8/8, was found to be 1.4±0.1 $min^{-1}$ at pH 7.6 and 25° C., which adjusted to pH 7.5 assuming a normal pH dependence, yields a rate constant of 1.1 $min^{-1}$, in good agreement with the published rate constant of 1.0 $min^{-1}$ under these conditions.

In hammerhead with the fully complementary substrates (OU CS), the usual trend of cleavage rate constant with helix I length was observed (OU RA-8/8+OU CS series), the cleavage rate constants peaked at a helix I length of 6 base pairs and decreased significantly on both sides of this peak.

When the shortened ribozyme was utilized with the complementary substrates (OU RA-6/8 +OU CA series) the rate constants increase with helix I length from 4 (2.5 $min^{-1}$) up to 6 base pairs (8 $min^{-1}$), then curiously although no further increase In helix I length was possible because it is limited by the length of the 5' arm on the ribozyme, increasing the length of the substrate, resulted in a significant decrease in observed cleavage rates (OU RA-6/8+OU CS-18-8/8; $k_{obs}$=4.3 $min^{-1}$). While the rate does not decline to the extent observed for the symmetric ribozyme (OU RA-8/8+OU CS-18-8/8; $k_{obs}$=0.71 $min^{-1}$), it is a significant fall off. It is mirrored by the difference in cleavage rate constant of OU CS-15-8/6 for OU RA-6/8 (8.0 $min^{-1}$) and OU RA-8/8 (3.9 $min^{-1}$). This suggests that in this particular system there is a kinetic penalty to be paid by having either ribozyme or substrate overhang at the end of helix I. This is probably related to the potential for formation of alternate (inactive) structures.

Alternative Conformational Flexibility

The fact that in vitro cleavage is observed in cases where both helices I and III are very long (Homann, et al. 1993; Lo, et al. 1992) suggests the presence of an alternate path for the ribozyme-substrate complex to achieve the active conformation. It may be possible, for example, that helix II is able to loosen enough to allow the conformational change. In support of this hypothesis, we have observed that minizymes (ribozymes lacking helix II) with 10 nucleotides in each hybridising arm invariably cleave symmetrical 21-mer substrates more efficiently than symmetrical 13-mer substrates, moreover no improvement in cleavage rate constants is observed for these minizymes cleaving 10/5 substrates compared with 10/10 substrates (where there are 5 and 10 base pairs, respectively, in helices I of the complexes). Thus the conformational flexibility possessed by the minizymes, because of their lack of helix II, allows them to attain the active conformation without dissociation of helix I.

Other Work

Denman et al (Denman, et al. 1995) have studied a number of ribozymes targeted to the β-amyloid peptide precursor (β-APP), with the expressed goal of investigating the effect of destabilising helix I. In their study, which was apparently complicated by multiple substrate conformations, the observed cleavage rates were very low. They concluded that the most active ribozyme was one with helices I and III of 7 and 8 base pairs respectively. Amiri and Hagerman (Amiri, et al. 1994) claim that a pre-annealed ribozyme with very long helices I and II, is able to cleave its annealed substrate with a rate constant of more than 5 $min^{-1}$ at pH 8, 25° C., upon the addition of 10 mM $MgCl_2$. However the accompanying figure (FIG. 2 in Amiri, et al. 1994) appears to show cleavage under those conditions with a rate constant of around 0.5 mm.

Ribozyme Design

There are very clear implications for ribozyme design in this study. or optimum in vitro cleavage rates, the 5' hybridising arm should contain in the order of 5±1 nucleotides. The number of nucleotides in the 3' hybridising arm, is less critical; however there should greater than about 5 nucleotides. If multiple turnovers are required, then the rate of dissociation of the 5' product of cleavage from the 3' arm of the ribozyme (i.e. the rate of dissociation of helix III after cleavage) also must be considered.

TABLE 1

Cleavage rate constants for symmetric 13- and 21-nucleotide substrates by their cognate ribozymes with 10/10 hybridising arms.

| | S13-6/6 | | S21-10/10 | |
|---|---|---|---|---|
| Ribozyme | III/I[a] | $k_{obs}$ | III/I[a] | $k_{obs}$ |
| GH RA-10/10[b] | 6/6 | 1.6 ± 0.6 | 10/10 | 0.5 ± 0.2 |
| GH RB-10/10[b] | 6/6 | 5 ± 1 | 10/10 | 1.9 ± 0.2 |
| TAT RA-10/10[c] | 6/6 | 0.24 ± 0.05 | 10/10 | 0.6 ± 0.1 |
| TAT RB-10/10[c] | 6/6 | 4.5 ± 0.3 | 10/10 | 0.44 ± 0.07 |
| Kr RA-10/10[c] | 6/6 | 9 ± 3 | 10/10 | 0.62 ± 0.03 |
| Kr RB-10/10[c] | 6/6 | 7.6 ± 0.6 | 10/10 | 2.7 ± 1.6 |

Conditions: pH 8.00, 10 mM $MgCl_2$
[a]number of base pairs in helices III and I respectively
[b]at 30° C.
[c]at 37° C.

TABLE 2

Cleavage rate constants for asymmetric 16-mer substrates by their cognate ribozymes with 10/10 hybridising arms.

| Ribozyme/Substrate | III/I | $k_{obs}$ ($min^{-1}$) | ratio $k_{obs}$ (10/5)/(5/10) |
|---|---|---|---|
| TAT RA-10/10[a] | | | |
| TAT S16-10/5 | 10/5 | 0.083 ± 0.006 | |
| TAT S16-5/10 | 5/10 | 0.15 ± 0.01 | 0.55 |

TABLE 2-continued

Cleavage rate constants for asymmetric 16-mer substrates by their cognate ribozymes with 10/10 hybridising arms.

| Ribozyme/Substrate | III/I | $k_{obs}$ ($min^{-1}$) | ratio $k_{obs}$ (10/5)/(5/10) |
|---|---|---|---|
| TAT RB-10/10[a] | | | |
| TAT S16-10/5 | 10/5 | 9 ± 2 | |
| TAT S16-5/10 | 5/10 | 0.068 ± 0.002 | 132 |
| Kr RA-10/10[b] | | | |
| Kr S16-10/5 | 10/5 | 4.6 ± 0.1 | |
| Kr S16-5/10 | 5/10 | 0.06 ± 0.01 | 77 |
| Kr RB-10/10[b] | | | |
| Kr S16-10/5 | 10/5 | 2.7 ± 0.6 | |
| Kr S16-5/10 | 5/10 | 0.10 ± 0.02 | 27 |

Conditions: 10 mM $MgCl_2$, 37° C.
[a]at pH 8.0
[b]at pH 7.13

TABLE 3

Cleavage rate constants for symmetric 21-nucleotide substrates by their cognate asymmetric ribozymes.

| Ribozyme | Substrate | III/I | $k_{obs}$ ($min^{-1}$) |
|---|---|---|---|
| TAT RA-10/5 | TAT S21-10/10 | 5/10 | 0.09 ± 0.01 |
| TAT RA-5/10 | TAT S21-10/10 | 10/5 | 10 ± 1 |
| Kr RA-6/10 | Kr S21-10/10 | 10/6 | 6.7 ± 0.1 |

Conditions: 10 mM $MgCl_2$, 37° C., pH 7.13.

TABLE 4

Effect of length of helix III on cleavage rate constants.

| Ribozyme | III/I | $k_{obs}$ ($min^{-1}$) S17-10/6 | III/I | $k_{obs}$ ($min^{-1}$) S13-6/6 |
|---|---|---|---|---|
| TAT RB-10/10 | 10/6 | 1.8 ± 0.4 | 6/6 | 0.92 ± 0.1 |
| Kr RA-10/10 | 10/6 | 4.8 ± 0.6 | 6/6 | 3.4 ± 1.0 |
| Kr RB-10/10 | 10/6 | 3.2 ± 0.3 | 6/6 | 1.7 ± 0.4 |

Conditions: 10 mM $MgCl_2$, 37° C., pH 7.13.

TABLE 5

| Ribozyme | Substrate | III/I | $k_{obs}$ ± sd($min^{-1}$) |
|---|---|---|---|
| OU RA-8/8 | OU S-13-8/4 | 8/4 | 1.0 ± 0.2 |
| OU RA-8/8 | OU S-14-8/5 | 8/5 | 0.27 ± 0.08 |
| OU RA-8/8 | OU S-15-8/6 | 8/6 | 1.2 ± 0.1 |
| OU RA-8/8 | OU S-16-8/7 | 8/7 | 2.4 ± 0.1 |
| OU RA-8/8 | OU S-18-8/8 | 8/8 | 1.4 ± 0.1 |
| OU RA-8/8 | OU CS-13-8/4 | 8/4 | 1.36 ± 0.01 |
| OU RA-8/8 | OU CS-15-8/5 | 8/5 | 3.4 ± 0.2 |
| OU RA-8/8 | OU CS-15-8/6 | 8/6 | 3.9 ± 0.1 |
| OU RA-8/8 | OU CS-16-8/7 | 8/7 | 2.5 ± 0.1 |
| OU RA-8/8 | OU CS-16-8/8 | 8/8 | 0.71 ± 0.01 |
| OU RA-6/8 | OU S-13-8/4 | 8/4 | 2.4 ± 0.3 |
| OU RA-6/8 | OU S-14-8/5 | 8/5 | 2.5 ± 0.4 |
| OU RA-6/8 | OU S-15-8/6 | 8/6 | 5.9 ± 0.8 |
| OU RA-6/8 | OU S-16-8/7 | 8/7 | 6.3 ± 0.5 |
| OU RA-6/8 | OU S-18-8/8 | 8/8 | 5.0 ± 0.4 |
| OU RA-6/8 | OU CS-13-8/4 | 8/4 | 2.7 ± 0.2 |
| OU RA-6/8 | OU CS-14-8/5 | 8/5 | 5.3 ± 0.8 |
| OU RA-6/8 | OU CS-15-8/6 | 8/6 | 8.0 ± 0.1 |
| OU RA-6/8 | OU CS-16-8/7 | 8/7 | 6.1 ± 0.1 |
| OU RA-6/8 | OU CS-18-8/8 | 8/8 | 4.3 ± 0.5 |

Conditions: 10 mM $MgCl_2$, 25° C., pH 7.60.

REFERENCES

Amiri, K. M. A. and Hagerman, P. J. (1994) *Biochemistry*, 33: 13172–13177.

Aurup, H., Williams, D. M. & Eckstein, F. (1992), *Biochemistry*, 31:9636–9641.

Augustyns, K., F. Vandendriessche, A. A. Van, R. Busson, C. Urbanke and P. Herdewijn. (1992), *Nucleic Acids Res.* 20:4711–6.

Bassi, G. S., Mollegaard, N. E., Murchie, A. I. H., Vonkitzing, E. and Lilley, D. M. J. (1995) *Nature Struct. Bioloqy*, 2: 45–55.

Beaton, G., Dellinger, D., Marshal, W. S. and Caruthers M. H. *Oligonucleotides and Analogues; a Practical Approach* pp 109–136, F. Eckstein (Ed). Oxford University Press, Oxford.

Beigelman, L., Karpeisky, A., Matulicadamic, J., Gonzalez, C., & Usman, N. (1995A), *Nucleos Nucleot.*, 14: 907–910.

Beigelman, L., Karpeisky, A., Matulicadamic, J., Haeberli, P., Sweedler, D., & Usman, N. (1995B) *Nucleic Acids Res.*, 23: 4434–4442.

Beijer, B., Grotli, M., Douglas, M. E. and Sproat, B. S. (1994), *Nucleos Nucleot.*, 13:1905–1927.

Bennett, C. F. et al. (1992) *Molecular Pharmacology* 41:1023–1033.

Blommers, M. J., U. Pieles and A. De Mesmaeker (1994), *Nucleic Acids Res.*, 22:4187–4194.

Bonfils, E. et al. (1992), *Nucleic Acids Res.*, 20:4621–4629.

Boutorin, A. S. (1989) FEBS Lett. 254:129–132.

Bracht et al. (1994) *Biochem Biophys Res. Commun.* 200: 1933–1937.

Bracht et al. (1995) *Agents Actions Supp.* 45: 315–322.

Bryant, J. (1992), *Tibtech,* 10:342–343.

Bunnell, B. A. et al. (1992) Somatic Cell Mol. Genetics 18:559–569.

Buzayan, J. M., W. L. Gerlach and G. Bruening. (1986). Non-enzymic cleavage and ligation of RNAs complementary to a plant virus satellite RNA. *Nature.* 323:349–53.

Buzayan, J. M., van Tol, H., Feldstein, P. A. and Breuning, G. (1990), *Nucleic Acids Res.*, 18:4447–4451. Phosphate 5' to A9 cannot be phosphorothioate.

Cao, X. and M. D. Matteucci (1994), *Tet. Lett.*, 35:2325–2328.

Carruthers, M. H. (1987), *Methods in Enzymology,* 154: 287–313).

Caruthers, M. H. (1991), *Nucleic Acids Research Symp Ser.* (ENGLAND), 24:91–94.

Caulfield, T. J., Prasad, C. V. C., Prouty, C. P., Saha, A. K., Sardaro, M. P., Schairer, W. C., Yawman, A., Upson, D. A., Kruse, L. I. (1994), *Bioorg. Med. Chem. Lett.,* 3:2771–2776.

Chen, J. K., R. G. Schultz, D. H. Lloyd and S. M. Gryaznov (1995), *Nucleic Acids Res.*, 23(14):2661–2668.

Chur, A., B. Holst, O. Dahl, H. P. Valentin and E. B. Pedersen (1993), *Nucleic Acids Res.*, 21(22):5179–83.

Conrad, F. (1995), *Nucleic Acids Res.*, 23:1845–1853.

Cotten, M. (1990), *Tibtech,* 8:174–178.

Debart, F., Rayner, B., Degols, G., & Imbach, J-L. (1992A), *Nucleic Acids Res.*, 20:1193–1200.

Debart, F., J. J. Vasseur, Y. S. Sanghvi and P. D. Cook. (1992B), *Bioorg. Med. Chem. Lett.,* 2:1479–1482.

De Mesmaeker, A., J. Lebreton, A. Waldner, V. Frisch, R. M. Wolf and S. M. Freier (1993), *Synlett,* 733–736.

De Mesmaeker, A., J. Lebreton, A. Waldner, V. Frisch and R. M. Wolf. (1994A), *Bioorg. Med. Chem. Lett.,* 4:873–878.

De Mesmaeker, A., A. Waldner, J. Lebreton, P. Hoffmann, V. Frisch, R. M. Wolf and S. M. Freier. (1994B), *Angew. Chem. Irt. Ed.,* 33:226–229.

De Mesmaeker, A., A. Waldner, Y. S. Sangvhi and J. Lebreton. (1994C), *Bioorg. Med. Chem. Lett.,* 4:395–398.

De Mesmaeker, A., A. Waldner, Y. S. Sangvhi and J. Lebreton. (1994D), *Bioorg. Med. Chem. Lett.,* 4:395–398.

De Mesmaeker, A., Altmann, K. H., Waldner, A., Wenderborn, S. (1995), *Current Opinion in Structural Biology,* 5:343–355.

Denman, R. B., M. Smedman and L. Kung. (1995). Differential activity of trans-acting hammerhead ribozymes targeted to beta amyloid peptide precursor mRNA by altering the symmetry of helices I and III. *Arch Biochem Biophys.* 323:71–78.

Egholm, M., O. Buchardt, L. Christensen, C. Behrens, S. M. Freier, D. A. Driver, R. H. Berg, S. K. Kim, B. Norden and P. E. Nielsen. (1993), *Nature,* 365:566–8.

Egholm, M., O. Buchardt, P. E. Nielsen and R. H. Berg. (1992A), *J. Am. Chem. Soc.*, 114:1895–1897.

Egholm, M., P. E. Nielsen, O. Buchardt and R. H. Berg. (1992B), *J. Am. Chem. Soc.*, 114:9677–9678.

Eldrup, A. B., K. Bjergarde, J. Felding, J. Kehler and O. Dahl. (1994), *Nucleic Acids Res.*, 2296(1082):1797–1804.

Ellis, J. and J. Rogers. (1993). Design and specificity of hammerhead ribozymes against calretinin mRNA. *Nucleic Acids Res.* 21:5171–5178.

Fathi, R., Q. Huang, G. Coppola, W. Delaney, R. Teasdale, A. M. Krieg and A. F. Cook. (1994A), *Nucleic Acids Res.* 22(24): 5416–5424.

Fathi, R., Q. Huang, J. L. Syi, W. Delaney and A. F. Cook. (1994B), *Bioconjug. Chem.* 5(1):47–57.

Fedor, M. and O. C. Uhlenbeck. (1992). Kinetics of Intermolecular cleavage by hammerhead ribozymes. *Biochemistry.* 31:12042–12054.

Fenster (1994), *Biochemistry.* 33: 8391–8398.

Foehler et al. (1986) *Nucleic Acids Res.* 14: 5399–407).

Friedman, T., (1989) *Science* 244: 1275–1280.

Froehler, B., P. Ng and M. Matteucci. (1988), *Nucleic Acids Res.*, 16(11): 4831–9.

Fu, D. J. and L. W. McLaughlin. (1992A), *Proc. Natl. Acad. Sci. USA.* 89(9): 3985–9. (G5, G8 can't be DNA. A6 and A9 can be DNA. G5 can't be inosine. G8 can be inosine, and A6 and A9 can be purine.)

Fu, D.-J. and McLaughlin, L. W. (1992B), *Biochemistry,* 31, 10941–10949. (Can't change atom N(7) to C(7) in A6; but can change N(7) to C(7) in A9, A13, A14, A15.1.) Fu, D.-J., S. B. Rajur and L. W. McLaughlin. (1993), *Biochemistry.* 32: 10629–10637.

Fu, D.-J. and L. W. McLaughlin. (1992), *Biochemistry.* 31: 10941–10949.

Garbesi, A., M. L. Capobianco, F. P. Colonna, L. Tondelli, F. Arcamone, G. Manzini, C. W. Hilbers, J. M. Aelen and M. J. Blommers. (1993), *Nucleic Acids Res.* 21: 4159–65.

Gast, F.-U., Amiri, K. M. A., & Hagerman, P. J. (1994), *Biochemistry* 33: 1788–1796.

Goodchild, J. (1992), *Nucleic Acids Res.* 20:4607–4612. (2'-O-methylation in hybridizing arms enhances cleavage and improves resistance to nucleases.)

Grasby, J. A., P. Jonathan, G. Butler and M. J. Gait. (1993), *Nucleic Acids Res.* 21(19): 4444–50.

Gryaznov, S. M. and R. L. Letsinger. (1992A), *Nucleic Acids Res.* 20(13): 3403–9.

Gryaznov, S. M. and R. L. Letsinger. (1992B), *Nucleic Acids Res.* 20(13): 3403–9.

Gryaznov, S. M., D. H. Lloyd, J. K. Chen, R. G. Schultz, L. A. DeDionisio, L. Ratmeyer and W. D. Wilson. (1995), *Proc. Natl. Acad. Sci. USA* 92(13): 5798–5802.

Green, R., and Szostak, J. W. (1992) *Science* 258:1910.

Hertel, K. J., Pardi, A., Uhlenbeck, O. C. Koizumi, M., Ohtsuka, E., Uesugi, S., Cedergren, R., Eckstein, F., Gerlach, W. L., Hodgson, R. & Symons, R. H. (1992) "A numbering system for the hammerhead ribozyme" *Nucleic Acids Res.,* 20, 3252.

Hertel, K. J., Herschlag, D. & Uhlenbeck, (1994) "A kinetic and thermodynamic framework for the hammerhead ribozyme reaction" *Biochemistry,* 33, 3374–3385.

Hertel, K. J., Herschlag, D. & Uhlenbeck, O. C. (1996) "Specificity of hammerhead ribozyme cleavage" The *EMBO Journal,* 15, 3751–3757.

Habus, I., J. miemsamani and S. Agrawal. (1994), *Biorg. Med. Chem. Lett.* 4: 1065–1070.

Hanvey, J. C., N. J. Peffer, J. E. Bisi, S. A. Thomson, R. Cadilla, J. A. Josey, D. J. Ricca, C. F. Hassman, M. A. Bonham, K. G. Au, S. G. Carter, D. A. Brukenstein, A. C. Boyd, S. A. Noble, L. E. Babiss (1992), *Science.* 258 (5087): 1481–5.

Haseloff, J. and W. L. Gerlach. (1988). Simple RNA enzymes with new and highly specific endoribonuclease activites. *Nature.* 334: 585–91.

Heidenreich, O. and Eckstein, F. (1992),*J. Biol. Chem.,* 267: 1904–1909. (2'-fluorocytidine substitutions have no effect on cleavage rates, but 2'-fluorouridine substitutions cause 5-fold decrease in $k_{cat}/K_M$. One 5' terminal and three 3' terminal phosphorothioate groups have little effect on rates. Putting all pyrimidines as 2'-fluoropyrimidines, and using the one 5' terminal and three 3' terminal phosphorothioate groups, gave a 7-fold reduction in $k_{cat}/K_M$, and 50-fold improvement in stability.) Heidenreich, O., Benseler, F., Fahrenholz, A. and Eckstein, F. (1994), *J. Biol. Chem.* 269: 2131–2138.

Hendry, P., M. J. McCall, F. S. Santiago and P. A. Jennings. (1992). A ribozyme with DNA in the hybridising arms displays enhanced cleavage ability. *Nucleic Acids Res.* 20: 5737–5741.

Hendry, P. et al (1994), *Biochim et Bioihys Acta,* 1219: 405–412.

Hendry, P. & McCall, M. J. (1995) "A comparison of the intro activity of DNA-armed and all-RNA hammerhead Ribozymes" *Nucl. Acids. Res.* 23: 3928–3936.

Hertel, K. J., D. Herschlag and O. C. Uhlenbeck. (1994). A kinetic and thermodynamic framework for the hammerhead ribozyme reaction. Biochemistry. 33: 3374–3385.

Hogan, B. et al., (1989), *Science,* 244: 1275.

Homann, M., S. Tzortzakaki, K. Rittner, G. Sczakiel and M. Tabler. (1993). Incorporation of the catalytic domain of a hammerhead ribozyme into antisense RNA enhances its inhibitory effect on the replication of human immunodeficiency virus type 1. *Nucleic Acids Res.* 21: 2809–14.

Heizenga et al. (1995) *Biochemistry* 34: 656–665.

Hutchins, C. J., P. D. Rathjen, A. C. Forster and R. H. Symons. (1986). Self-cleavage of plus and minus RNA transcripts of avocado sunblothc viroid. *Nucleic Acids Res.* 14: 3627–3640.

Idsiak, I., G. Just, M. J. Damha and P. A. Gianaris. (1993), *Tet. Lett.* 34: 5417–5420.

Kabanov, A. V. (1990) FEBS Lett. 259:327–330.

Jager, A., M. J. Levy and S. M. Hecht. (1988), *Biochemistry.* 27(19): 7237–46.

Jones, R. J., K. Y. Lin, J. F. Milligan, S. Wadwani and M. D. Matteucci. (1993), *J. Org. Chem.* 58: 2983–2991.

Lematre, M. et al. (1987) Proc. Natl. Acad. Sci. USA 84:648–652.

Lebreton, J., A. De Mesmaeker, A. Waldner, V. Fritsch, R. Wolf and S. M. Freier. (1993), *Tet. Lett.* 34: 6383–6386.

Lebreton, J., A. Waldner, C. Lesueur and A. De Mesmaeker. (1994A), *Synlett,* 137–140.

Lebreton, J., A. Waldner, V. Fritsch, R. M. Wolf and A. De Mesmaeker. (1994B), *Tet. Lett.* 35: 5223–5228.

Leonetti, J. P. et al. (1990) Proc. Natl. Acad. Sci. USA 87:2448–2451.

Letsinger, R. L., Singman, C. N., Histand, G., Salunkhe, M. (1988), *J. Am. Chem. Soc.,* 110: 4470–4471.

Letsinger, R. L. (1989) Proc. Natl. Acad. Sci USA 86:6553–6556.

Lo, K. M., M. A. Biasolo, G. Dehni, G. Palu and W. A. Haseltine. (1992). Inhibition of replication of HIV-1 by retroviral vectors expressing tat-antisense and anti-tat ribozyme RNA. *Virology.* 190: 176–83.

Loke, S. L. et al. (1988) Top. Microbiol. Immunol. 141: 282–289.

Maliga, P. 1993) *Tibtech* 11:101–106.

Matteucci, M. D. (1990), *Tet. Lett.* 31:2385–2388.

McCall, M. J., P. Hendry and P. A. Jennings. (1992). Minimal sequence requirements for ribozyme activity. *Proc Natl Acad Sci USA.* 89: 5710–5714.

Miller P. S., Bahn, P., Cushman, C D., Kean, J. M., Levis, J. T. (1991), *Nucleosides and Nucleotides,* 10: 27–46.

Monia, B. P., E. A. Lesnik, C. Gonzalez, W. F. Lima, D. McGee, C. J. Guinosso, A. M. Kawasaki, P. D. Cook and S. M. Freier. (1993), *J. Biol. Chem.* 268(19): 14514–22.

Ng, M. M. P., F. Benseler, T. Tuschl and F. Eckstein. (1994), *Biochemistry* 33(40): 12119–12126.

Nielsen, P. E., M. Egholm, R. H. Berg and O. Buchardt. (1993A), *Anticancer Drug Des.* 8(1): 53–63.

Nielsen, P. E., M. Egholm, R. H. Berg and O. Buchardt. (1993B), *Nucleic Acids Res.* 21(2): 197–200.

Oberhauser, B. (1992) Nucleic Acids Res. 20:533–538.

Odai, O., Hiroaki, H., Sakata, T., Tanaka, T. and Uesugi, S. (1990), *FEBS Lett.* 267: 150–152. (G5 cannot be inosine; the 2-amino group seems to be important for stability.)

Olsen, D. B., F. Benseler, H. Aurup, W. A. Picken and F. Eckstein. (1991), *Biochemistry* 30:9735–9741. (Single 2'-fluoro or 2'-H (DNA) substitutions on adenosines have little effect on cleavage, but results are additive, so that cleavage drops as more modifications are added. 2'deoxy or 2'-fluoro modifications at A6 and A9 are OK; A13-A15.1 are more sensitive.)

Paclella, G., Sproat, B. S. and Lamond, A. I. (1992), *The EMBO Journal* 11: 1913–1919. (Can make all nucleotides 2'-O-allyl ribonucleotides except U4, G5, A6, 08, G12, A15.1. Of these six ribonucleotides, either U4 or A6, but not both, may be 2'-O-allyl, without much loss in activity, but better activity is achieved if U4 and A6 are unmodified RNA. With U4, G5, A6, G8 and A15.1 as RNA and other nucleotides 2'-O-allyl, G12 can be DNA.)

Partridge, W. M. et al. (1993) Drug Delivery 1:43–50.

Partridge, W. M. (1991) FEBS Lett. 288:30–32.

Perreault, J.-P., Wu, T., Cousineau, B., Ogilvie, K.K. and Cedergren, R. (1990), *Nature,* 344: 565–567. (Putting DNA into conserved nucleotides A6, G8, A9, G12, A13 and A14 reduces activity, but doesn't eliminate it Making G5 as DNA results in big reduction in activity.)

Perreault, J.-P., Labuda, D., Usman, N., Yang, J.-H. and Cedergren, R. (1991), *Biochemistry,* 30: 020–4025. (G5 and A9 cannot be DNA. G12, A13, A14, G8 can be DNA.)

Perriman, R., A. Delves and W. L. Gerlach. (1992). Extended target-site specificity for a hammerhead ribozyme. *Gene.* 113: 157–63.

Perriman, R., et al. (1993) *Antisense Res. & Dev.* 3:253–263.

Pieken, W. A., Olsen, D. B., Aurup, H., Williams, D. M., Heidenreich, O., Benseler, F., and Eckstein, F. (1991), *Nucleic Acids Res. Symposium Series,* 24. (2'amino group at C15.2 (together with 3 other 2'-amino Cs in hybridizing arms) has reduction in activity. Can't have 2'-amino at G5, but can at G12.)

Pieken, W. A., Olsen, D. B., Benseler, F., Aurup, H. and Eckstein, F. (1991), *Science,* 253: 314–317. (Can make all cytidines (C3, 15.2) and uridines U4, U7) 2'-fluoro or 2'-amino and noc get much reduczion in cleavage activity. A9 can be 2'-fluoro, but A13, A14 and A15 together cannot have 2'-fluoro group.).

Pley, H. W., Flaherty, K. M. and Mckay, D. B. (1994) *Nature,* 372: 68–74.

Ruffner, D. E. and Uhlenbeck, O. C. (1990) *Nucleic Acids Res.,* 18: 6025–6029.

Saenger, W. (1984), *Principles of Nucleic Acid Structure,* Springer-Verlag, N.Y.

Sambrook, J. et al., (1989), *Molecular Cloning, A Laboratory Manual,* 2nd Edizion, Cold Spring Harbor Press.

Scott, W. G., Finch, J. T. and Klug, A. (1995) *Cell,* 81: 991–1002.

Seela, F., K. Mersmann, J. A. Grasby and M. J. Gait. (1993). *Helv. Chim. Acta.* 76: 1809–1820.

Setlik, R. F., Shibata, M., Sarma, R. H., Sarma, M. H., Kazim, A. L., Ornstein, R. L., Tomasi, T. B. and Rein, R. (1995) *J. Biomol. Struct. Dyn.,* 13: 515–522.

Shaw, J.-P., Kent, K., Bird, J., Fishback, J. and Froehler, B. (1991) *Nucleic Acids Res.,* 19:747–750. (Degradation of oligodeoxynucleotides in fetal calf serum and cell supernatant is predominantly by 3'exonucleases. Good protection from these 3'exonucleases (and little change in melting temperatures of duplexes) is achieved by synthesizing oligodeoxyribonucleotides with one or two methoxyethyleneamine(MEA) phosphoroamidate substitutions at the 3' end, or by an inverted linkage (3'—3') using an inverted diester or an inverted phosphoroamidate. Uniformly substituted phosphorothioate oligonucleotides were also very stable to 3'exonucleases, but melting temperatures of duplexes were lowered by 10° C.)

Shea R. G. et al. (1990) Nucleic Acids Res. 18:3777–3783.

Shimamoto, K., Terada, R., Izawa, T., and Fujimoto, H. (1989) *Nature* 338:274–276.

Shimayama, T., F. Nishikawa, S. Nishikawa and K. Taira. (1993). Nuclease resistant chimeric ribozymes containing deoxyribonucleotides and phosphorothioate linkages. *Nucleic Acids Res.* 21: 2605–2611.

Shimayama, T. (1994) *Gene,* 149: 41–46.

Shimayama, T., S. Nishikawa and K. Taira. (1995). Generality of the NUX rule: Kinetic analysis of the results of systematic mutations in the trinuclectide at the cleavage site of hammerhead ribozymes. *Biochemistry.* 34: 3649–3654.

Sinha, N. D., Biernat, J, & Koster, H. (1984) *Nucleic Acids Res.* 12: 4539–4557.

Slim, G. and M. Gait. (1992). *Biochem. Biophys. Res. Commun.* 183: 605–609.(G12 cannot be inosine; A13, A15.1 cannot be purine. A14 can be purine. G8 can be inosine (but rates down 10-fold) and A9 can be purine (but rates down 6-fold).).

Sober, H. (1970), CRC Handbook of Biochemistry, Second edition.

Sproat et al. *Oligonucleotide Synthesis—A Practical Approach,* IRL Press, Oxford (1984) M. J. Gait—Editor, pp. 83–115).

Sproat, B. S. and Lamond, A. I. (1991A) 2'-O-methyloligoribonucleotides: Synthesis and applications. in *Oligonucleotides and Analogues; a Practical Aproach* pp 49–86, F. Eckstein (Ed). Oxford University Press, Oxford.

Sproat, B. S., A. I. Lamond, R. G. Garcia, B. Beijer, U. Pieles, M. Douglas, K. Bohmann, F. M. Carmo, S. Weston and S. O'Loughlin. (1991B) . *Nucleic Acids Symp Ser.* 1991 (24). 59–62.

Stec, W. J.; Grajkowski, A.; Koziolkiewicz, M.; Uznanski, B. (1991). *Nucleic Acids Res.* 19, 5883–8.

Stec, W. J., Grajkowski, A., Kobylanska, A., Karwowski, B., Koziolkiewicz, M., Misiura, K., Okruszek, A., Wilk, A., Guga, P., & Boczkowska, M. (1995) *J. Am. Chem. Soc.* 117, 12019–12029.

Stirchak, E. P., J. E. Summerton and D. D. Weller. (1987). *J. Org. Chem.* 52 4202–4206.

Sullenger, B. A. and Cech, T. R. (1993) *Science* 262:1566–1569.

Strobel, S. A. et al., (1991), *Nature* 350: 172–174 and references therein.

Stull, R. A. and Szoka, F. C. (1995) Pharmaceutical research 12: 465–483.

Summers, M. F., C. Powell, W. Egan, R. A. Byrd, W. D. Wilson and G. Zon. (1986). *Nucleic Acids Res.* 14(18). 7421–36.

Symons, R. H. (1992). Small catalytic RNAs. *Ann. Rev. Biochem.* 61, 641–671.

Tabler, M., M. Homann, S. Tzortzakaki and G. Sczakiel. (1994). A three-nucleotide helix I is sufficient for full activity of a hammerhead ribozyme: advantages of an asymmetric design. *Nucleic Acids Res.* 22, 3958–3965.

Tuschl, T. & Eckstein, F., (1993), *Proc. Nat. Acad. Sci. USA,* 90:6991–6994.

Tuschl, T., M. M. P. Ng, W. Pieken, F. Benseler and F. Eckstein. (1993). *Biochemistry.* 32(43). 11658–11668.

Uhlenbeck, O. C. (1987). A small catalytic oligoribonucleotide. *Nature.* 328, 596–600.

Uhlmann et al., (1990), *Chem. Revs.,* 90:544–584.

Usman, N., Beigelman, L., Draper, K., Wincott, F and McSwiggen, J. (1995) RNA synthesis and ribozymes. *J. Cellular Biochemistry,* Abstract supplement 19A, Abstract A6-018, p 205.

Vasseur, J. J., F. Debart, Y. S. Sanghvi and P. D. Cook. (1992). *J. Am. Chem. Soc.* 114: 4006–4007.

Waldner, A., A. De Mesmaeker and J. Lebreton. (1994A). *Bioorg. Med. Chem. Lett.* 4: 405–408.

Waldner, A. and A. De Mesmaeker. (1995). *Synlett.* 108–110.

Waldner, A., A. De Mesmaeker, J. Lebreton, V. Fritsch and R. M. Wolf. (1994B). *Synlett.* 57–61.

Werner, M. and O. C. Uhlenbeck. (1995). The effect of base mismatches in the substrate recognition helices of hammerhead ribozymes on binding and catalysis. *Nucleic Acids Res.* 23: 2092–2096.

Williams, D. M., Pieken, W. A. and Eckstein, F. (1992) *Proc. Natl. Acad. Sci. USA,* 89: 918–921. (G5 and G8 cannot have 2'F, 2'H, or 2'amino (reduction in k(cat) is about 150-fold for 2'F, 2'H, and about 10-fold for 2'amino). G12 can have 2'H and 2'amino, but cannot have 2'F.)

Yang, J.-H., J. P. Perreault, D. Labuda, N. Usman and R. Cedergren, (1990) *Biochemistry* 29: 11156–11160.

Yang, J.-H., Usman, N., Chartrand, P. and Cedergren, R. (1992) *Biochemistry,* 31: 5005–5009. (DNA is OK at C3, T4, A6, T7, G12, A13, A14. Can't have DNA at G5, A15.1. If lots of sites are DNA, then rates drop dramatically if G8 is DNA or G1S.2 is DNA.)

Zoumadakis, M. and M. Tabler. (1995). Comparative analysis of cleavage rates after systematic permutation of the NUX consensus target motif for hammerhead ribozymes. *Nucleic Acids Res.* 23: 1192–1196.

Zoumadakis, M., W. J. Neubert and M. Tabler. (1994). The influence of imperfectly paired helices I and III on the catalytic activity of hammerhead ribozymes. *Nucleic Acids Res.* 22: 5271–5278.

We claim:

1. A compound having the formula:

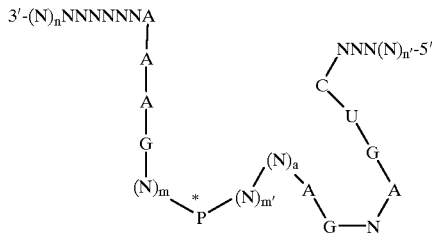

wherein each N represents a nucleotide which may be the same or different and may be substituted or modified in its sugar, base or phosphate provided not every N is a ribonucleotide;

wherein 3'-(N)$_n$NNNNNNA and NNN(N)$_{n'}$-5' represent oligonucleotide segments of the compound consisting of a predetermined sequence which hybridizes with an RNA target sequence to be cleaved, wherein if either of 3'-(N)$_n$NNNNNNA or NNN(N)$_{n'}$-5' is covalently linked at its respective 3' and 5' termini to an additional nucleotide, then that additional nucleotide is not complementary to the RNA target sequence;

wherein each of n and n' represents an integer which defines the number of nucleotides with the proviso that n is from 2 to 5 and n' is 2 or 3, or n=1 and n'=2;

wherein each * represents base pairing between the nucleotides located on either side thereof;

wherein each solid line represents a chemical linkage providing covalent bonds between the nucleotides located on either side thereof;

wherein a represents an integer which defines a number of nucleotides with the proviso that a may be 0 or 1 and if 0, the A located 5' of (N)$_a$ is bonded to the N located 3' of (N)$_a$;

wherein each m and m' represents an integer which is greater than 2; wherein P represents a non-nucleotide linker or a nucleotide linker (N)$_b$ and wherein (N)$_b$ represents an oligonucleotide which may be present with the proviso that b represents an integer which is greater than or equal to 3.

2. The compound of claim 1, wherein the oligonucleotide segment 3'-(N)$_n$NNNNNNA is 3'-(N)$_n$NNNNNCA.

3. The compound of claim 1, wherein (N)$_a$ is absent.

4. The compound of claim 1, wherein the integer b of (N)$_b$ is equal to 4.

5. The compound of claim 1, wherein each of m and m' are 4.

6. The compound of claim 1 wherein each N is a deoxyribonucleotide.

7. The compound of claim 1 wherein each N of 3' (N)$_n$NNNNNNA and NNN(N)$_{n'}$' 5' is a deoxyribonucleotide.

8. The compound of claim 1 wherein several of the nucleotides N, A, C, G or U are 2'-O-alkyl ribonucleotides.

9. The compound of claim 8 wherein the 2'-O-alkyl ribonucleotides are 2'-O-methyl ribonucleotides.

10. The compound of claim 1 covalently linked to a moiety that serves as a cellular delivery agent.

11. The compound of claim 10, wherein the delivery agent is a peptide, a peptide mimic, a cholesterol, a steroid, a cholesterol derivative, a fat, a vitamin, biotin, folic acid, retinoic acid, a protein, ferritin, LDL, insulin, an antibody, a sugar or an oligosaccharide, polyethylene glycol or a homopolymer or co-polymer of aminoacids.

12. The compound of claim 1, wherein the RNA target sequence is a viral RNA target sequence.

13. A composition which comprises a compound of claim 1 in association with a carrier.

14. The composition of claim 13, wherein the carrier comprises cationic lipids, cholesterol, cholesterol derivatives, a homopolymer or a co-polymer of amino acids or liposomes.

15. A host cell comprising the compound of claim 1, wherein the host cell is a prokaryotic host cell or an eukaryotic host cell.

16. The prokaryotic host cell of claim 15, wherein the prokaryotic host cell is an E. coli host cell.

17. The eukaryotic host cell of claim 15, wherein the eukaryotic host cell is a monkey COS host cell, a Chinese hamster ovary host cell, a mammalian host cell, a plant host cell or yeast cell.

18. A diagnostic reagent which comprises the compound of claim 1.

* * * * *